US011545691B2

(12) United States Patent
Guarr

(10) Patent No.: US 11,545,691 B2
(45) Date of Patent: Jan. 3, 2023

(54) REDOX FLOW BATTERY

(71) Applicant: Board of Trustees of Michigan State University, East Lansing, MI (US)

(72) Inventor: Thomas F. Guarr, Holland, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 411 days.

(21) Appl. No.: 16/628,496

(22) PCT Filed: Jul. 20, 2018

(86) PCT No.: PCT/US2018/043048
§ 371 (c)(1),
(2) Date: Jan. 3, 2020

(87) PCT Pub. No.: WO2019/018741
PCT Pub. Date: Jan. 24, 2019

(65) Prior Publication Data
US 2020/0136165 A1 Apr. 30, 2020

Related U.S. Application Data

(60) Provisional application No. 62/671,117, filed on May 14, 2018, provisional application No. 62/534,781, filed on Jul. 20, 2017.

(51) Int. Cl.
| | | |
|---|---|---|
| *C07D 401/04* | (2006.01) | |
| *C07D 401/06* | (2006.01) | |
| *C07D 401/10* | (2006.01) | |
| *C07D 401/14* | (2006.01) | |
| *C07D 417/04* | (2006.01) | |
| *C07D 417/06* | (2006.01) | |
| *C07D 417/10* | (2006.01) | |
| *C07D 417/14* | (2006.01) | |
| *H01M 8/18* | (2006.01) | |
| *H01M 4/36* | (2006.01) | |
| *H01M 4/60* | (2006.01) | |

(52) U.S. Cl.
CPC .......... *H01M 8/188* (2013.01); *C07D 401/04* (2013.01); *C07D 401/06* (2013.01); *C07D 401/10* (2013.01); *C07D 401/14* (2013.01); *C07D 417/04* (2013.01); *C07D 417/06* (2013.01); *C07D 417/10* (2013.01); *C07D 417/14* (2013.01); *H01M 4/368* (2013.01); *H01M 4/60* (2013.01)

(58) Field of Classification Search
CPC ........ H01M 8/188; H01M 4/368; H01M 4/60; C07D 401/04; C07D 401/06; C07D 401/10; C07D 401/14; C07D 417/04; C07D 417/06; C07D 417/10; C07D 417/14

See application file for complete search history.

(56) References Cited

U.S. PATENT DOCUMENTS

| | | |
|---|---|---|
| 2,944,058 A | 7/1960 | Kallischnigg et al. |
| 3,896,145 A | 7/1975 | Berger et al. |
| 5,976,731 A | 11/1999 | Negoro et al. |
| 6,207,292 B1 | 3/2001 | Berneth et al. |
| 6,241,916 B1 | 6/2001 | Claussen et al. |
| 6,249,369 B1 | 6/2001 | Theiste et al. |
| 6,445,486 B1 | 9/2002 | Lomprey et al. |
| 6,545,793 B2 | 4/2003 | Berneth et al. |
| 7,615,312 B2 | 11/2009 | Dahn et al. |
| 7,615,317 B2 | 11/2009 | Dahn et al. |
| 7,811,710 B2 | 10/2010 | Dahn et al. |
| 7,851,092 B2 | 12/2010 | Amine et al. |
| 8,367,253 B2 | 2/2013 | Chen et al. |
| 8,384,068 B2 | 2/2013 | Kahle et al. |
| 8,609,287 B2 | 12/2013 | Zhang et al. |
| 9,209,476 B2 | 12/2015 | Knuckey et al. |
| 10,535,824 B2 | 1/2020 | Wang et al. |
| 2002/0197486 A1 | 12/2002 | Berneth et al. |
| 2005/0221196 A1 | 10/2005 | Dahn et al. |
| 2006/0257746 A1 | 11/2006 | Inagaki et al. |
| 2006/0263697 A1 | 11/2006 | Dahn et al. |
| 2007/0020479 A1 | 1/2007 | Uetani et al. |
| 2007/0196727 A1 | 8/2007 | Wang et al. |

(Continued)

FOREIGN PATENT DOCUMENTS

| | | |
|---|---|---|
| CN | 101595591 A | 12/2009 |
| CN | 101921262 A | 12/2010 |

(Continued)

OTHER PUBLICATIONS

English language abstract for JP2013501337 extracted from espacenet.com database on Jun. 17, 2021, 1 page.
English language abstract for JP2012214671 extracted from espacenet.com database on Jun. 17, 2021, 1 page.
English language abstract and machine-assisted English translation for JP2004101729 extracted from espacenet.com database on Jun. 17, 2021, 15 pages.
English language abstract and machine-assisted English translation for JP2015115110 extracted from espacenet.com database on Jun. 17, 2021, 32 pages.
English language abstract and machine-assisted English translation for JP2016033117 extracted from espacenet.com database on Jun. 17, 2021, 23 pages.

(Continued)

*Primary Examiner* — Timothy R Rozof
(74) *Attorney, Agent, or Firm* — Howard & Howard Attorneys PLLC

(57) ABSTRACT

A redox flow battery includes a cathode, an anode, a charge-carrying electrolyte, and an (a) oxidized and a (b) reduced form of an active material. The active material has the following formula: $(D)-(L)-(A)-[(L)-(A)]_v-D_z(F1)$ or $(D)-(L)-(A)-(L-D)_X(F2)$. In these formulae, each D is covalently bonded to an L, each L is covalently bonded to an A, x is a number from 0 to 5, v is a number from 0 to 5 and z is 0 or 1. D is an electron donor compound, L is a linker, and A is an electron acceptor compound. Each of D, L, and A has a particular structure.

29 Claims, 1 Drawing Sheet

(56) References Cited

U.S. PATENT DOCUMENTS

| | | | |
|---|---|---|---|
| 2008/0014496 | A1 | 1/2008 | Watanabe et al. |
| 2009/0042103 | A1 | 2/2009 | Xiao et al. |
| 2010/0068621 | A1 | 3/2010 | Exnar et al. |
| 2010/0187980 | A1 | 7/2010 | Langer et al. |
| 2010/0297480 | A1 | 11/2010 | Martinent et al. |
| 2011/0006738 | A1 | 1/2011 | Mikhaylik et al. |
| 2011/0079773 | A1 | 4/2011 | Wasielewski et al. |
| 2011/0244319 | A1 | 10/2011 | Hashimoto |
| 2011/0294019 | A1 | 12/2011 | Amine et al. |
| 2013/0288137 | A1 | 10/2013 | Weng et al. |
| 2014/0178756 | A1 | 6/2014 | Ishii et al. |
| 2015/0372333 | A1 | 2/2015 | Odom et al. |
| 2015/0108451 | A1* | 4/2015 | Thompson .......... H01L 51/0091 548/103 |
| 2015/0248969 | A1 | 9/2015 | Watanabe et al. |
| 2017/0062842 | A1 | 3/2017 | Huang et al. |
| 2017/0162916 | A1 | 6/2017 | Guarr et al. |
| 2019/0305381 | A1 | 10/2019 | Guarr et al. |

FOREIGN PATENT DOCUMENTS

| | | |
|---|---|---|
| CN | 101921262 A | 12/2010 |
| DE | 1152107 A | 8/1963 |
| DE | 1152107 B | 8/1963 |
| DE | 19605451 A1 | 8/1997 |
| DE | 19605451 A1 | 8/1997 |
| DE | 19631728 A1 | 2/1998 |
| DE | 19631728 A1 | 2/1998 |
| DE | 19735732 A1 | 2/1999 |
| DE | 19735732 A1 | 2/1999 |
| DE | 19735733 A1 | 2/1999 |
| DE | 19735733 A1 | 2/1999 |
| DE | 19801638 A1 | 7/1999 |
| DE | 19801638 A1 | 7/1999 |
| EP | 0 827 230 A2 | 3/1998 |
| EP | 0889037 A1 | 1/1999 |
| FR | 2866478 A1 | 8/2005 |
| GB | 818269 A | 8/1959 |
| GB | 2507661 A | 5/2014 |
| JP | H08195199 A | 7/1996 |
| JP | H10134845 A | 5/1998 |
| JP | H10144347 A | 5/1998 |
| JP | 2001023687 A | 1/2001 |
| JP | 2004101729 A | 4/2004 |
| JP | 2007522628 A | 8/2007 |
| JP | 2009272170 A | 11/2009 |
| JP | 2012214671 A | 11/2012 |
| JP | 2013501337 A | 1/2013 |
| JP | 2015-086201 A | 5/2015 |
| JP | 2015-086202 A | 5/2015 |
| JP | 2015115110 A | 6/2015 |
| JP | 2016033117 A | 3/2016 |
| JP | 2016-103417 A | 6/2016 |
| WO | 99/09111 A1 | 2/1999 |
| WO | 2009102604 A1 | 8/2009 |
| WO | 2009/141288 A2 | 11/2009 |
| WO | 2014/093225 A2 | 6/2014 |
| WO | 2016/011393 A1 | 1/2016 |
| WO | 2018/098116 A2 | 5/2018 |
| WO | 2019/018741 A1 | 1/2019 |

OTHER PUBLICATIONS

English language abstract and machine-assisted English translation for JPH08195199 extracted from espacenet.com database on Jun. 17, 2021, 12 pages.

Non-Final Office Action (U.S. Appl. No. 16/462,419); dated Oct. 9, 2020; 20 pages.

Non-Final Office Action (U.S. Appl. No. 16/269,009); dated Nov. 24, 2020; 23 pages.

Odom, Susan et al.; "Synthesis and analysis of redox shuttles for overcharge protection in lithium-ion batteries", 1 page.

Adachi, Momoe et al., "Aromatic Compounds at Redox Shuttle Additives for 4 V Class Secondary Lithium Batteries" J. Electrochem. Soc. 1999, vol. 146(4)m pp. 1256-1261.

Buhrmester, Claudia et al., "Phenothiazine Molecules-Possible Redox Shuttle Additives for Chemical Overcharge and Overdischarge Protection for Lithium-Ion Batteries", J. Electrochem.Soc, 2006, vol. 153(2), pp. A288-A294.

Zhang, Lu et al., "Novel Redox Shuttle Additive for High-Voltage Cathode Materials", Energy Environ. Sci., vol. 4, 2011, pp. 2858-2862.

Zhang, Lu et al., "Lithium Ion Batteries—New Developments", Chapter 7—Redox Shuttle Additives for Lithium-Ion Battery, Chapter 7, Feb. 2012, pp. 173-188.

Zhang, Lu et al., "Molecular Engineering Towards Safer Lithium-Ion Batteries: a Highly Stable and Compatible Redox Shuttle for Overcharge Protection", Energy Environ. Sci, vol. 5, 2012, pp. 8204-8207.

Odom, Susan et al.; "Increasing redox shuttle oxidation potentials to match high voltage cathodes in lithium-ion batteries", 1 page.

Ergun, Selin et al.; "Overcharge performance of 3,7-disubstituted N-ethylphenothiazine derivatives in lithium-ion batteries", The Royal Society of Chemistry, 3 pages, Nov. 11, 2013.

Odom, Susan et al.; "A fast, inexpensive method for predicting overcharge performance in lithium-ion batteries", The Royal Society of Chemistry, 8 pages, Nov. 11, 2013.

Narayana, Klishore et al.; "N-substituted phenothiazine derivatives as electrolyte additives for overcharge protection in lithium-ion batteries", 1 page.

Narayana, Kishore Anand et al.; "N-Substituted Phenothiazine Derivatives: How the Stability of the Neutral and Radical Cation Forms Affects Overcharge Performance in Lithium-Ion Batteries", 11 pages.

Casselman, Matthew et al.; "The fate of phenothiazine-based redox shuttles in lithium-ion batteries", 8 pages, Jan. 22, 2015.

International Search Report and Written Opinion ; Office Action (PCT Application No. PCT/US2015/040970); dated Jan. 5, 2016; 19 pages.

Kaur, Aman Preet et al.; "Overcharge protection of lithium-ion batteries above 4 V with a perfluorinated phenothiazine derivative", 5 pages, Mar. 10, 2016.

Sevov, Christo S. et al., "Physical Organic Approach to Persistent, Cyclable, Low-Potential Electrolytes for Flow Battery Applications", J. A,/ Chem Soc., vol. 139, No. 8, 2017, pp. 2924-2927.

International Search Report and Written Opinion; Office Action (PCT Appication No. PCT/US17/62698); dated Feb. 2, 2018; 9 pages.

International Search Report and Written Opinion; Office Action (PCT Application No. PCT/US18/43048); dated Sep. 17, 2018; 16 pages.

Notification of Reasons for Refusal; Office Action (JP Application No. 2017-502961); dated Jun. 24, 2019; 9 pages; Includes English Translation.

The Second Office Action (CN Application No. 201580050272.5); dated Sep. 17, 2019; 5 pages.

Examination Report No. 1 (AU Application No. 2018302335); dated Apr. 24, 2020; 9 pages.

Examination Report No. 2 (AU Application No. 2018302335); dated May 28, 2020; 3 pages.

Notice of Acceptance (AU Application No. 2018302335); dated Jul. 3, 2020; 3 pages.

Deronzier, Alain et al., "Polymeric Films Containing Acceptor-Donor Assemblies", J. Phys. Chem. 1991, 95, pp. 1737-1742.

Tu, Xi et al. "The Synthesis and Electrochemical Properties of Cathodic-Anodic Composite Electrochromic Material", Dyes and Pigments 88 (2011), pp. 39-43.

English language abstract and original Polish language document of Morak-Mlodawska, B et al., "New Derivatives of Phenothiazines with Anticancer Activities" Polski merkuriusz lekarski: organ Polskiego Towarzystwa Lekarskiego, Jul. 2009, vol. 126, No. 156, pp. 671-675.

Kurihara, T. et al. Relationship Between Cytotoxic Activity and Dipole Moment for Phthalimido- and Chloroethyl-Phenothiazines, May 11, 1999, pp. 4081-4083.

(56) References Cited

OTHER PUBLICATIONS

Koyuncu, Fatma Baycan et al. "A Novel Donor-Acceptor Polymeric Electrochromic Material Containing Carbazole and 1,8-naphtalimide as Subunit." Electrochimica Acta, Mar. 30, 2010, pp. 4935-4941.

Kirankuma, R. et al. Multifunctional Electropolymerizable Carbazole-based Ionic Liquids, Royal Society of Chemistry Adcances, vol. 6, 2015, pp. 15735-15744.

Lim, Jee Young et al. Single and Dual-Type Electrochromic Devices Based on Polycarbazole Derivative Bearing Pendent Viologen, Synthetic Metals, vol. 156, 2006, pp. 695-698.

Winsberg, Jan et al., "Redox-Flow Batteries: From Metals to Organic Redox-Active Materials," Angew. Chem. Int. Ed., vol. 56, 2017, pp. 686-711.

English language abstract and machine-assisted English translation for DE19801638A1 extracted from the espacenet.com database on Jul. 6, 2022, 46 pages.

English language abstract and machine-assisted English translation for CN101921262A extracted from the espacenet.com database on Jul. 6, 2022, 23 pages.

English language abstract not found for DE1152107B; however, see English language equivalent U.S. Pat. No. 2,944,058A. Original document extracted from espacenet.com database on Jul. 7, 2022, 6 pages.

English language abstract for DE19631728A1 extracted from espacenet.com database on Jul. 7, 2022, 1 page.

English language abstract for DE19735732A1 extracted from espacenet.com database on Jul. 7, 2022, 1 page.

English language abstract for DE19735733A1 extracted from espacenet.com database on Jul. 7, 2022, 1 page.

English language abstract for DE19605451A1 extracted from espacenet.com database on Jul. 7, 2022, 1 page.

\* cited by examiner

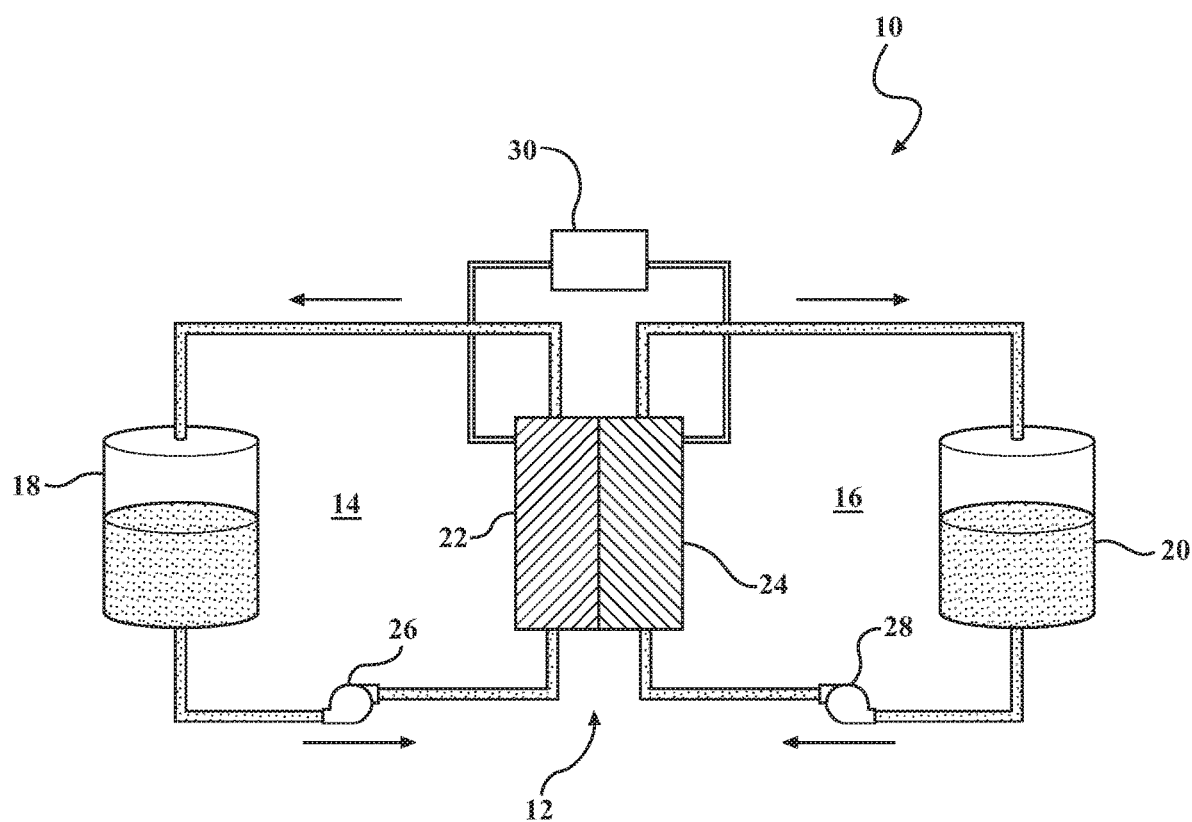

REDOX FLOW BATTERY

CROSS-REFERENCE TO RELATED APPLICATIONS

This application is a National Stage of International Patent Application No. PCT/US2018/043048, filed on Jul. 20, 2018, which claims the benefit of U.S. Provisional Patent Application No. 62/534,781, filed on Jul. 20, 2017 and U.S. Provisional Patent Application No. 62/671,117, filed on May 14, 2018 the contents of which are incorporated herein by reference.

FIELD OF THE DISCLOSURE

The present disclosure relates generally to a device for storing electrical energy and, more particularly, to a redox flow battery. More specifically, the redox flow battery includes a particular active material.

BACKGROUND

A redox flow battery is an energy storage device designed to store electrical energy produced from oxidized and reduced chemical species. Redox flow batteries typically have an electrochemical cell containing at least two electrodes and at least two electroactive materials. Each of the electroactive materials is typically in the form of an electrolyte solution or slurry, including an electroactive material, a suitable solvent, and optionally an electrolyte salt for improved ionic conductivity. The electrolyte solutions may be moved from respective storage receptacles through the electrochemical cell using a pump, gravity, pressure, or other suitable means.

Electrochemical cells are typically divided into an anode and a cathode chamber by an ion exchange or microporous membrane that serves to minimize mixing of the different electroactive materials. Mixing of the electroactive materials is often referred to as "crossover" or "cross-contamination". During use, the electrolyte salt anion and/or cation are transported across the membrane, which facilitates an electrochemical reaction between the electroactive materials to produce energy.

The material(s) for the ion exchange or microporous membrane is/are often expensive, and the membrane typically requires regular maintenance or replacement. In addition, membranes are typically somewhat inefficient, which can lead to mixing of the different electroactive materials. For at least these reasons, replacement of the electroactive materials may be required over time.

Currently, there are certain redox flow battery designs that do not utilize an ion exchange or microporous membrane. Such designs, however, rely on laminar flow techniques, which are often inefficient and impractical for real world applications. Such designs also employ overly expensive materials, materials that are difficult to control, and materials that are sensitive to environmental changes, which further complicates the widespread deployment of such redox flow battery designs. Accordingly, there remains an opportunity for improvement.

SUMMARY

The present disclosure provides a redox flow battery that includes a cathode, an anode, a charge-carrying electrolyte, and an (a) oxidized and a (b) reduced form of an active material. The active material has the following formula:

$$(D)-(L)-(A)-[(L)-(A)]_v-D_Z \quad \text{(F1)}$$

or $$(D)-(L)-(A)-(L-D)_X \quad \text{(F2)}$$

In these formulae, each D is covalently bonded to an L, each L is covalently bonded to an A, x is a number from 0 to 5, v is a number from 0 to 5 and z is 0 or 1. Moreover, D is an electron donor compound, L is a linker, and A is an electron acceptor compound. Each D has the following structure (D1):

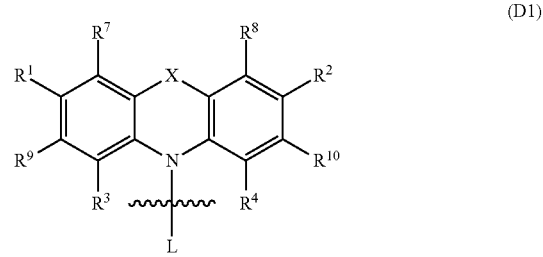

wherein X is a covalent bond, a sulfur atom (S), $SO_2$, or N—$R^6$, and wherein each of $R^1$, $R^2$, $R^3$, $R^4$, $R^6$, $R^7$, $R^8$, $R^9$ and $R^{10}$ is independently a hydrogen atom, an alkyl group, a nitrile group, a haloalkyl group, a perhaloalkyl group, an acyl group, and acyloxy group, an acetyl group, a haloacetyl group, an alkylaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, an arylhaloalkyl group, a methylsulfonyloxyl group, a nitro group, an alkyl ether group, a haloalkylether group, a trialkylammoniumalkyl group, a phosphate group, a phosphonate group, or an alkyl phosphonate group. Moreover, each L is chosen from an alkyl group having 2 to 6 carbon atoms, an aromatic group, and a direct bond. Furthermore, each A has the following structure (A1) or (A2) or (A3) or (A4) or (A5):

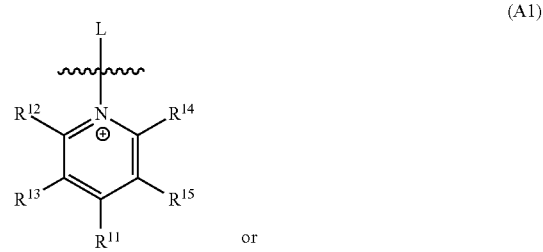

or

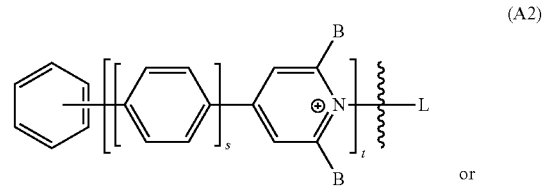

or (A3)

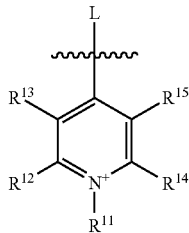

or (A4)

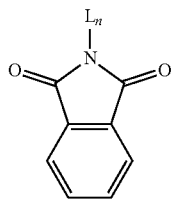

or (A5)

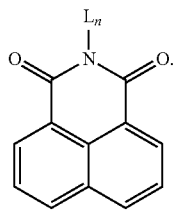

wherein each of $R^{12}$ and $R^{14}$ is a phenyl group, a hydrogen atom, or an alkyl group having 1 to 6 carbon atoms, and wherein each of $R^{13}$ and $R^{15}$ is a hydrogen atom or an alkyl group having 1 to 6 carbon atoms. In addition, $R^{11}$ is chosen from a hydrogen atom, an alkyl group, an acetyl group, an aryl group, a substituted aryl group, or a group having the following structure (P1) or (P2):

(P1)

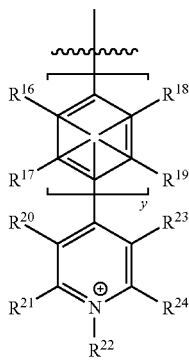

(P2)

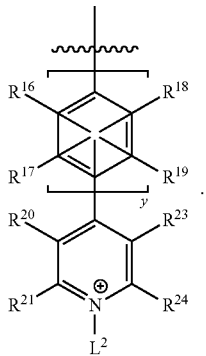

In (P1) and (P2), y is a number from 0 to 4, each of $R^{16}$-$R^{19}$ is a phenyl group, a hydrogen atom, or an alkyl group having 1 to 6 carbon atoms, each of $R^{21}$, $R^{22}$, and $R^{24}$ is a phenyl group, a hydrogen atom, or an alkyl group having 1 to 6 carbon atoms, each of $R^{20}$ and $R^{23}$ is a hydrogen atom or an alkyl group having 1 to 6 carbon atoms, and L2 is optionally a second linker. Moreover, in (A2), s is a number from 0 to 2, t is a number from 1 to 6, and each B is a hydrogen atom, an alkyl group having 1 to 6 carbon atoms, or an aryl or substituted aryl group.

The present disclosure also provides a redox flow battery comprising a cathode, an anode, a charge-carrying electrolyte, and an active material comprising two or more pyridine or substituted pyridine units, any two of which are separated by 1 to 3 phenyl or substituted phenyl groups. One or more of the pyridine or substituted pyridine units are linked through a nitrogen atom to a moiety having a reversible electrochemical oxidation.

The present disclosure also provides an active material for a redox flow battery with the active material having the following formula:

$$(D)\text{-}(L)\text{-}(A)\text{-}[(L)\text{-}(A)]_{v}\text{-}D_{Z} \quad \text{(F1)}$$

or $$(D)\text{-}(L)\text{-}(A)\text{-}(L\text{-}D)_{X} \quad \text{(F2)}$$

Each D is covalently bonded to an L, wherein each L is covalently bonded to an A, wherein x is a number from 0 to 5, v is a number from 0 to 5 and z is 0 or 1, wherein D is an electron donor compound, L is a linker, and A is an electron acceptor compound.

Each D has the following structure (D1):

(D1)

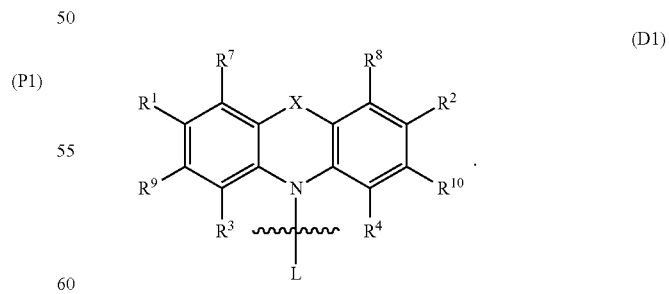

X is a covalent bond, a sulfur atom (S), $SO_2$, or N—$R^6$, and wherein each of $R^1$, $R^2$, $R^3$, $R^4$, $R^6$, $R^7$, $R^8$, $R^9$ and $R^{10}$ is independently a hydrogen atom, an alkyl group, a nitrile group, a haloalkyl group, a perhaloalkyl group, an acyl group, and acyloxy group, an acetyl group, a haloacetyl group, an alkylaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, an arylhaloalkyl group, a methylsulfonyloxyl group, a nitro group, an oxo group, an alkyl ether group, a haloalkylether group, a trialkylammoniumalkyl group, a phosphate group, a phosphonate group, or an alkyl phosphonate group.

Each L is chosen from an alkyl group having 2 to 6 carbon atoms, an aromatic group, and a direct bond, and each A has the following structure (A1) or (A2) or (A3) or (A4) or (A5):

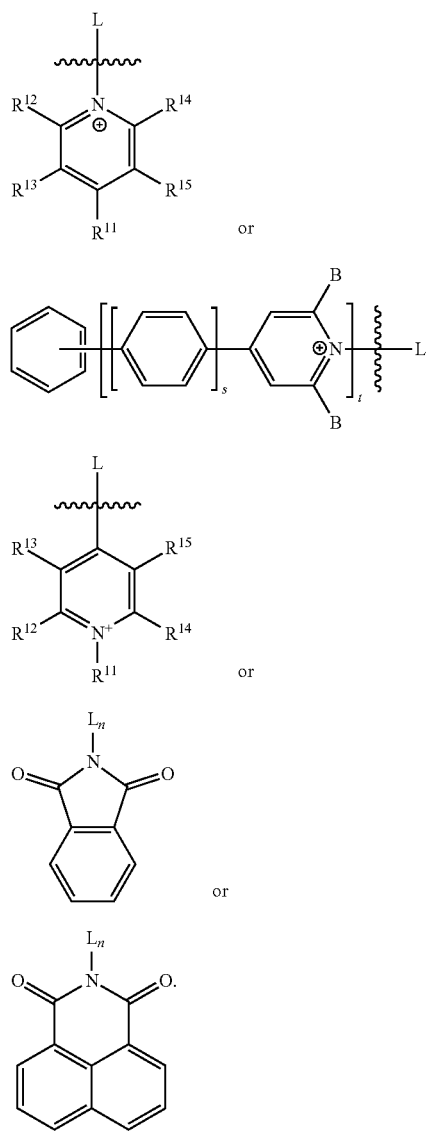

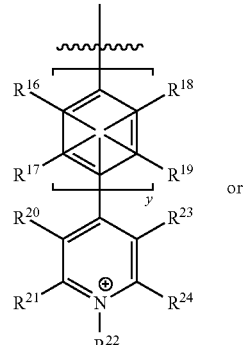

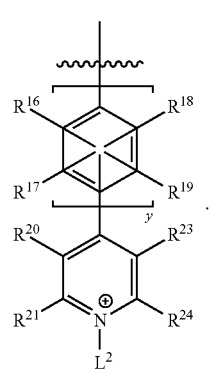

Wherein y is a number from 0 to 4; wherein each of $R^{16}$-$R^{19}$ is a phenyl group, a hydrogen atom, or an alkyl group having 2 to 6 carbon atoms; wherein each of $R^{21}$, $R^{22}$, and $R^{24}$ is a phenyl group, a hydrogen atom, or an alkyl group having 1 to 6 carbon atoms, wherein each of $R^{20}$ and $R^{23}$ is a hydrogen atom or an alkyl group having 1 to 6 carbon atoms; and wherein $L^2$ is optionally a second linker. In (A2), s is a number from 0 to 2, t is a number from 1 to 6, and each B is a hydrogen atom, an alkyl group having 1 to 6 carbon atoms, or an aryl or substituted aryl group.

BRIEF DESCRIPTION OF THE DRAWING

The advantages of the present disclosure will be readily appreciated as the same becomes better understood by reference to the following detailed description when considered in connection with the accompanying drawing. It is to be understood that the drawing is purely illustrative and not necessarily drawn to scale.

The FIGURE is a schematic illustration of redox flow battery according to one non-limiting embodiment of the present disclosure.

DETAILED DESCRIPTION

With reference to the drawing, the FIGURE illustrates a redox flow battery 10 according to an embodiment of the present disclosure. The redox flow battery 10 may be described as an energy storage device that utilizes redox (reduction and oxidation) reactions to generate energy, which is stored in electrolyte solutions flowing through the battery 10. During discharge of the battery 10, electrons are released during an oxidation reaction on the negative (or anode) side of the battery 10. The electrons move through an external circuit to do useful work, and are thereafter accepted during a reduction reaction at the positive (or For each of (A1), (A2), and (A3), each of $R^{12}$ and $R^{14}$ is a phenyl group, a hydrogen atom, or an alkyl group having 1 to 6 carbon atoms, and each of $R^{13}$ and $R^{15}$ is a hydrogen atom or an alkyl group having 1 to 6 carbon atoms, and $R^{11}$ is chosen from a hydrogen atom, an alkyl group, an acetyl group, an aryl group, a substituted aryl group, or a group having the following structure (P1) or (P2):

cathode) side of the battery 10. The direction of the current and the chemical reactions are reversed during charging. The energy produced by the redox flow battery 10 is often used for grid storage applications. It is to be appreciated, however, that the redox flow battery 10 can be scaled to fit the needs of any suitable application.

Turning to the FIGURE, the redox flow battery 10 has an electrochemical cell 12 including a positive (cathode) side 14 and a negative (anode) side 16. The positive side 14 has a first receptacle 18 containing a charge carrying electrolyte and the oxidized form of an electroactive material (herein referred to as an active material), and the negative side 16 has a second receptacle 20 containing the charge carrying electrolyte and the reduced form of an electroactive material. The positive side 14 further includes a cathode 22, and the negative side further has an anode 24. The net charge in each receptacle is zero. Any positively charged species are balanced by a negative charged species, and vice versa.

During charging and discharging of the redox flow battery 10, the charge-carrying electrolyte on the positive side 14 circulates from the first receptacle 18 and through the cathode 22 by a first pump 26. The charge-carrying electrolyte on the negative side 16 circulates from the second receptacle 20 and through the anode 24 by a second pump 28. The cathode 22 and the anode 24 may be electrically connected through current collectors with an external load 30. As the electrolyte pass through the cathode 22 and the anode 24, the electroactive material reacts (via redox reaction(s)) to generate energy.

The cathode 22 may be one or a pair of electrodes or an array of electrodes that, under typical circumstances, has the highest potential it can achieve under normal operation. The anode 24 may be one or a pair of electrodes or an array of electrodes that, under normal circumstances, has the lowest potential it can achieve under normal operation. The cathode 22 and the anode 24 are not particularly limited and may be any known in the art. In a non-limiting example, one or more of the cathode 22 and the anode 24 is a carbon-based electrode, a metal-based electrode, and combinations thereof. Non-limiting examples of carbon-based electrodes include electrodes made or formed from porous carbon (e.g. carbon felt and graphite felt), carbon nanotubes, carbon nanowires, graphene, and/or the like, and/or combinations thereof. Non-limiting examples of metal-based electrodes include electrodes made or formed from gold, steel, nickel, platinum-coated gold, platinum-coated carbon, and/or the like, and/or combinations thereof. In another non-limiting example, the cathode 22 and/or the anode 24 is porous. The cathode 22 and/or anode 24 may further include additives, such as carbon black, flake graphite, and/or the like. Each of the cathode 22 and the anode 24 may be in any convenient form, including foils, plates, rods, screens, pastes, or as a composite made by forming a coating of the electrode material on a conductive current collector or other suitable support.

The charge-carrying electrolyte typically includes a charge-carrying medium and ions. The charge-carrying medium is not particularly limiting, and may be chosen from any medium that will suitably transport energy between the cathode 22 and the anode 24. In a non-limiting example, the charge-carrying medium may be one or more liquids and/or gels. In addition, the charge-carrying medium may be used over a wide temperature range, for example, from about −30° C. to about 70° C. without freezing or boiling, and is typically stable in the electrochemical window within which the cathode 22 and the anode 24 operate. Non-limiting examples of charge-carrying mediums include, but are not limited to, ethylene carbonate, propylene carbonate, dimethyl carbonate, diethyl carbonate, ethylmethyl carbonate, butylene carbonate, vinylene carbonate, fluoroethylene carbonate, fluoropropylene carbonate, γ-butyrolactone, methyl difluoroacetate, ethyl difluoroacetate, dimethoxyethane, diglyme (bis(2-methoxyethyl)ether), and/or combinations thereof. In various embodiments, the charge-carrying medium includes ethylene carbonate, propylene carbonate, dimethyl carbonate, diethyl carbonate, ethylmethyl carbonate, and/or combinations thereof.

The charge-carrying medium is typically present in an amount of from 40% to 99% by weight, from 60 to 99% by weight, from 65% to 95% by weight, or from 70% to 90% by weight, each based on a total weight of the charge-carrying electrolyte. All values and ranges of values within those values described above are hereby expressly contemplated in various non-limiting embodiments.

Referring now to the active material, the active material is typically incorporated into or carried by the charge-carrying electrolyte on both the positive 14 and negative 16 sides. In a fully charged redox flow battery 10, there is an (a) oxidized form of the active material present and a (b) reduced form of the active material present. There is little to none of the active material as shown below in the non-oxidized or non-reduced form. In a fully discharged (dead) redox flow battery 10, there is very little to none of the (a) oxidized form of the active material present and very little to none of the (b) reduced form of the active material present. Instead, all or almost all of the active material will be in the form as shown below in the non-oxidized or non-reduced form.

The active material may be present in any amount. In various embodiments, the active material is present in an amount of from 1 to 50, 5 to 45, 10 to 40, 15 to 35, 20 to 30, 25 to 30, 1, 2, 3, 4, 5, 6, 7, 8, 9, or 10, weight percent based on a total weight of the charge-carrying electrolyte. All values including and between those set forth above are hereby expressly contemplated in various non-limiting embodiments.

Active Material:

Referring now to the (a) oxidized and (b) reduced forms of the active material, the active material has the following formula:

$$(D)\text{-}(L)\text{-}(A)\text{-}[(L)\text{-}(A)]_v\text{-}D_z \quad \text{(F1)}$$

or $$(D)\text{-}(L)\text{-}(A)\text{-}(L\text{-}D)_x \quad \text{(F2)}$$

wherein each D is covalently bonded to an L, wherein each L is covalently bonded to an A, wherein x is a number from 0 to 6, v is a number from 0 to 5 and z is 0 or 1. In this formula, each D is an electron donor compound, each L is a linker, and each A is an electron acceptor compound. In this formula, x can be 0, 1, 2, 3, 4, or 5. Moreover, v can be 0, 1, 2, 3, 4, or 5.

For the sake of simplicity and referring to a basic D-L-A structure, on the positive side 14, the half reaction that typically occurs on the cathode 22 is shown in Equation 1:

$$D^+\text{-}L\text{-}A + e^- \rightarrow D\text{-}L\text{-}A \quad \text{(Eqn. 1)}.$$

On the negative side, the half reaction that typically occurs on the anode 24 is shown in Equation 2:

$$D\text{-}L\text{-}A^- + e^- \rightarrow D\text{-}L\text{-}A \quad \text{(Eqn. 2)}.$$

Since the product of the half-reactions shown in Equations 1 and 2 above are the same, cross-contamination of the spent active species typically does not occur. Accordingly, the redox flow battery 10 does not require an ion-exchange membrane or non-selective porous separator separating the cathode 22 and the anode 24. However, such a membrane or non-selective porous separator can be optionally used to prevent or minimize the chance of direct electrical shorting of the cathode 22 and anode 24, or as a fail-safe mechanism. In various embodiments, and unlike conventional redox flow batteries, the redox flow battery 10 is free of a membrane (such as selective membrane, an ion-selective membrane, or any membrane described above) that separates the cathode 22 and the anode 24. With this design, the electrolyte on the positive 14 and negative 16 sides can be introduced through the cathode 22 and the anode 24, respectively, and electron transfer occurs utilizing the external circuit. The redox flow battery 10 is reliably operated in the absence of the membrane that separates the cathode 22 and the anode 24. In the absence of a membrane, cross-contamination of the electrolyte on the positive 14 and negative 16 sides is minimized or prevented by providing a chemical linkage between the electron donor and acceptor groups of the active material.

Referring back to the active material itself, in one embodiment, per either (F1) or (F2), the formula is D-L-A, wherein v and z are each 0.

In another embodiment, per (F1), the formula is D-L-A-L-A-D, wherein v is 1 and z is 1.

In another embodiment, per (F1), the formula is D-L-A-L-A-L-A-D, wherein v is 2 and z is 1.

In another embodiment, per (F1), the formula is D-L-A-L-A-L-A-L-A-D, wherein v is 3 and z is 1.

In another embodiment, per (F1), the formula is D-L-A-L-A-L-A-L-A-L-A-D, wherein v is 4 and z is 1.

In another embodiment, per (F1), the formula is D-L-A-L-A-L-A-L-A-L-A-L-A-D, wherein v is 5 and z is 1.

In an alternative embodiments, per (F2), the formula is D-L-A-2L-D$_2$.

In an alternative embodiments, per (F2), the formula is D-L-A-3L-D$_3$.

In an alternative embodiments, per (F2), the formula is D-L-A-4L-D$_4$.

In an alternative embodiments, per (F2), the formula is D-L-A-5L-D$_5$.

All combinations of the aforementioned D, L, A, v, x and z are hereby expressly contemplated in various non-limiting embodiments. One or more (D) electron donor compounds in any embodiment herein can be any (D) electron donor compound described below. Similarly, one or more (L) linkers in any embodiment herein can be any (L) linker described below. Moreover, one or more (A) electron acceptor compounds in any embodiment herein can be any (A) electron acceptor compound described below. In other words, there may be two or more different (D), (L), and/or (A) in one active material.

Electron Donor Compound (D):

In various embodiments, one or more of the (D) electron donor compound has the following structure:

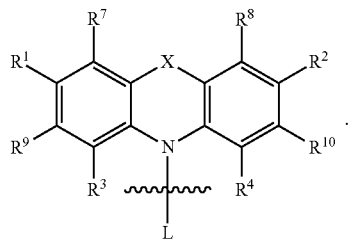

In this structure, X is a covalent bond, a sulfur atom (S), SO$_2$, or N—R$^6$, and wherein each of R$^1$, R$^2$, R$^3$, R$^4$, R$^6$, R$^7$, R$^8$, R$^9$ and R$^{10}$ is independently a hydrogen atom, an alkyl group, a nitrile group, a haloalkyl group, a perhaloalkyl group, an acyl group, and acyloxy group, an acetyl group, a haloacetyl group, an alkylaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, an arylhaloalkyl group, a methylsulfonyloxyl group, a nitro group, an alkyl ether group, a haloalkylether group, a trialkylammoniumalkyl group, a phosphate group, a phosphonate group, or an alkyl phosphonate group. Moreover, any one of R$^1$, R$^2$, R$^3$, R$^4$, R$^6$, R$^7$, R$^8$, R$^9$ and R$^{10}$ for any structure herein may be as described in greater detail below. Said differently, various non-limiting embodiments are hereby expressly contemplated wherein each of R$^1$, R$^2$, R$^3$, R$^4$, R$^6$, R$^7$, R$^8$, R$^9$ and R$^{10}$ are independently chosen as described in all sections below.

In various embodiments, each of R$^1$ and R$^2$ is independently an alkyl group, a haloalkyl group (including perhaloalkyl), or an alkyl ether group and at least one of R$^3$ and R$^4$ is an alkyl group, a haloalkyl group (including perhaloalkyl), an alkyl ether group, an acyl group, or a haloacyl group. Without intending to be bound by any particular theory, it is believed that substitution at these positions surprisingly increases the oxidation potential through a steric effect. In other embodiments, each of R$^1$, R$^2$, R$^3$, R$^4$, are chosen from alkyl groups, alkyl ether groups, acetyl groups, and CF$_3$ groups. Alternative electron donor compounds include substituted carbazoles, substituted 5,10-dihydrophenazines, and combinations thereof. In various embodiments, each of R$^3$ and R$^4$ are hydrogen atoms (e.g. R$^3$=R$^4$=H), no matter which structure is utilized.

In other embodiments, one or more of the (D) electron donor compound has the following structure:

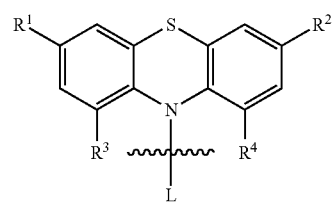

In various embodiments, each of R$^1$, R$^2$, R$^3$, and R$^4$, is independently an alkyl group, a haloalkyl group (e.g. mono-, di-, or tri-halo), a perhaloalkyl group, an acyl group, an acyloxy group, an acetyl group, a haloacetyl group, an alkaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, a methylsulfonyloxyl group, a nitro group, an alkyl ether group, a trialkylammoniumalkyl group, a phosphate group, a phosphonate group, or an alkyl phosphonate group. Alternatively, one of R$^3$ and R$^4$ is a hydrogen atom. In one embodiment, one of R$^3$ and R$^4$ is a hydrogen atom whereas the other of R$^3$ and R$^4$ is not a hydrogen atom.

In other embodiments, each of R$^1$ and R$^2$ is independently an alkyl group, a haloalkyl group (e.g. mono-, di-, or tri-halo), a perhaloalkyl group, an acyl group, an acyloxy group, an acetyl group, a haloacetyl group, an alkaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, a methylsulfonyloxyl group, a nitro group, an alkyl ether group, a trialkylammoniumalkyl group, a phosphate group, a phosphonate group, or an alkyl phosphonate group. In related embodiments, each of $R^3$ and $R^4$ is independently an alkyl group having 1-6 or 1-12 carbon atoms or a haloalkyl group (e.g. mono-, di-, or tri-halo) having 1 to 12 carbon atoms. Alternatively, one of $R^3$ and $R^4$ is a hydrogen atom. In one embodiment, one of $R^3$ and $R^4$ is a hydrogen atom whereas the other of $R^3$ and $R^4$ is not a hydrogen atom.

In further embodiments, each of $R^1$ and $R^2$ is independently an alkyl group having 1, 2, 3, 4, 5, or 6 carbon atoms or 1-12 carbon atoms, a trifluoromethyl group, a halo group, a cyano group, an alkyl ether group having 1 to 12 carbon atoms, an alkyl ether group having 1-12 carbon atoms, or a trialkylammoniumalkyl group having 1 to 12 carbon atoms. In other embodiments, each of $R^3$ and $R^4$ are independently an alkyl group having 1, 2, 3, 4, 5, or 6 carbon atoms or 1-12 carbon atoms, a haloalkyl group (e.g. mono-, di-, or tri-halo) having 1-6 or 1-12 carbon atoms, a perhaloalkyl group having 1-6 or 1-12 carbon atoms, an acyl group, a haloacyl group, or a perhaloacyl group. Non-limiting examples of suitable alkyl groups are methyl, ethyl, propyl, isopropyl, butyl, isobutyl, sec-butyl, tert-butyl, neopentyl, n-pentyl, hexyl, octyl, and the like, as appreciated by those of skill in the art. Alternatively, all values and ranges of values within those values described above are hereby expressly contemplated in various non-limiting embodiments.

In still other embodiments, each of $R^3$ and $R^4$ are sterically bulky. The terminology "sterically bulky" is appreciated by those of skill in the art. For example, each of $R^3$ and $R^4$ may be a $C_2$-$C_4$ alkyl group, such as an isopropyl, butyl, isobutyl, sec-butyl, or tert-butyl group. These types of groups may shift a potential to a more positive value without sacrificing (or at least minimizing an effect on) stability of the compound. Alternatively, each of $R^3$ and $R^4$ may be a $C_2$-$C_5$ alkyl group and may include those groups described above and neopentyl groups. In still other embodiments, each of $R^3$ and $R^4$ may be methyl and/or $CF_3$ groups. In some embodiments, relative to phenothiazines, 5,10-dihydrophenazines, and carbazoles, calculations show that a methyl groups, haloalkyl groups (e.g. mono-, di-, or tri-halo), and perhaloalkyl groups are sufficiently sterically bulky to induce a positive shift of the oxidation potential.

In various embodiments, each of $R^1$ and $R^2$ is independently an alkyl group, a haloalkyl group (including perhaloalkyl), or an alkyl ether group and at least one of $R^3$ and $R^4$ is an alkyl group, a haloalkyl group (including perhaloalkyl), an alkyl ether group, an acyl group, or a haloacyl group. In other embodiments, each of $R^1$, $R^2$, $R^3$, and $R^4$, are chosen from alkyl groups, alkyl ether groups, acetyl groups, and $CF_3$ groups. Without intending to be bound by any particular theory, it is believed that substitution at these positions surprisingly increases the oxidation potential through a steric effect.

In other embodiments, one or more of the (D) electron donor compound has one of the following structures:

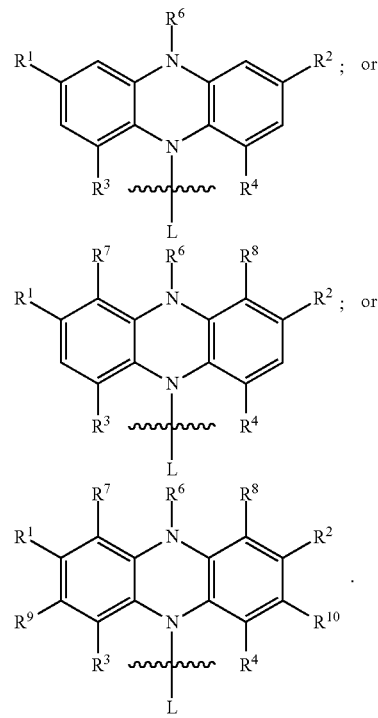

Without intending to be bound by any particular theory, it is believed that 5,10-dihydrophenazines have the lowest baseline oxidation potential, phenothiazines have a mid-level oxidation potential, carbazoles have a slightly higher baseline oxidation potential than phenothiazines, and phenothiazine-5,5-dioxides have the highest baseline oxidation potential. In various embodiments, steric effects of ortho substitution at the 1,8 positions of the carbazole may be relatively modest. In addition, steric effects of ortho substitution at the 1, 4, 6, 9 positions of 5,10-dihydrophenazine may be larger.

In these structures, each of $R^1$, $R^2$, $R^3$, $R^4$, $R^6$, $R^7$, and $R^8$ is independently an alkyl group, a haloalkyl group (e.g. mono-, di-, or tri-halo), a perhaloalkyl group, an acyl group, an acyloxy group, an acetyl group, a haloacetyl group, an alkaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, a methylsulfonyloxyl group, a nitro group, an oxo group, an alkyl ether group, a trialkylammoniumalkyl group, a phosphate group, a phosphonate group, or an alkyl phosphonate group. In one embodiment, one of $R^3$ and $R^4$ and/or one of $R^7$ and $R^8$ is a hydrogen atom whereas the other of $R^3$ and $R^4$ and/or $R^7$ and $R^8$ is not a hydrogen atom. Each of $R^9$ and $R^{10}$ may independently be the same or different from any one of RIL, $R^2$, $R^3$, $R^4$, $R^6$, $R^7$, and/or $R^8$ described above. In other embodiments, any or all of $R^{10}$, $R^2$, $R^9$, and $R^{10}$ can be H. Alternatively, one of $R^3$ and $R^4$ is a hydrogen atom. In one embodiment, one of $R^3$ and $R^4$ is a hydrogen atom whereas the other of $R^3$ and $R^4$ is not a hydrogen atom. In another embodiment, each of $R^3$ and $R^4$ and $R^7$ and $R^8$ is hydrogen.

In other embodiments, each of $R^1$ and $R^2$ is independently an alkyl group, a haloalkyl group (e.g. mono-, di-, or tri-halo), a perhaloalkyl group, an acyl group, an acyloxy group, an acetyl group, a haloacetyl group, an alkaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, a methylsulfonyloxyl group, a nitro group, an alkyl ether group, a trialkylammoniumalkyl group, a phosphate group, a phosphonate group, or an alkyl phosphonate group. In related embodiments, each of $R^3$ and $R^4$ is independently an alkyl group having 1 to 12 carbon atoms or a haloalkyl group (e.g. mono-, di-, or tri-halo) having 1 to 12 carbon atoms. Alternatively, one of $R^3$ and $R^4$ is a hydrogen atom. In one embodiment, one of $R^3$ and $R^4$ is a hydrogen atom whereas the other of $R^3$ and $R^4$ is not a hydrogen atom. In other embodiments, $R^6$ is independently an alkyl group having 1, 2, 3, 4, 5, or 6 carbon atoms or 1-12 carbon atoms, a haloalkyl group (e.g. mono-, di-, or tri-halo) having 1-6 or 1-12 carbon atoms, a perhaloalkyl group having 1-6 or 1-12 carbon atoms, an alkyl ether group having 1-12 carbon atoms, or a trialkylammoniumalkyl group. In still other embodiments, each of $R^7$ and $R^8$ are the same or different than $R^3$ and $R^4$, respectively. Alternatively, each of $R^7$ and $R^8$ can be any group described above relative to $R^3$ and/or $R^4$. Alternatively, all values and ranges of values within those values described above are hereby expressly contemplated in various non-limiting embodiments.

In further embodiments, each of $R^1$ and $R^2$ is independently an alkyl group having 1, 2, 3, 4, 5, or 6 carbon atoms or 1-12 carbon atoms, a trifluoromethyl group, a halo group, a cyano group, an alkyl ether group having 1 to 12 carbon atoms, or a trialkylammoniumalkyl group having 1 to 12 carbon atoms. In other embodiments, each of $R^3$ and $R^4$ are independently an alkyl group having 1, 2, 3, 4, 5, or 6 carbon atoms or 1-12 carbon atoms, a haloalkyl group (e.g. mono-, di-, or tri-halo) having 1-6 or 1-12 carbon atoms, a perhaloalkyl group having 1-6 or 1-12 carbon atoms, an acyl group, or a haloacyl group. Alternatively, all values and ranges of values within those values described above are hereby expressly contemplated in various non-limiting embodiments.

In still other embodiments, each of $R^3$ and $R^4$ are sterically bulky. The terminology "sterically bulky" is appreciated by those of skill in the art. For example, each of $R^3$ and $R^4$ may be a $C_2$-$C_4$ alkyl group, such as an isopropyl, butyl, isobutyl, sec-butyl, or tert-butyl group. These types of groups may shift a potential to a more positive value without sacrificing (or at least minimizing an effect on) stability of the compound. Alternatively, each of $R^3$ and $R^4$ may be a $C_2$-$C_5$ alkyl group and may include those groups described above and neopentyl groups. In still other embodiments, each of $R^3$ and $R^4$ may be methyl and/or $CF_3$ groups. Alternatively, one of $R^3$ and $R^4$ is a hydrogen atom. In one embodiment, one of $R^3$ and $R^4$ is a hydrogen atom whereas the other of $R^3$ and $R^4$ is not a hydrogen atom. In some embodiments, relative to phenothiazines, 5,10-dihydrophenazines, and carbazoles, calculations show that a methyl groups, haloalkyl groups (e.g. mono-, di-, or tri-halo) and perhaloalkyl groups are sufficiently sterically bulky to induce a positive shift of the oxidation potential.

In various embodiments, each of $R^1$ and $R^2$ is independently an alkyl group, a haloalkyl group (including perhaloalkyl), or an alkyl ether group and at least one of $R^3$ and $R^4$ is an alkyl group, a haloalkyl group (including perhaloalkyl), alkyl ether group, an acyl group, or a haloacyl group. In other embodiments, each of $R^1$, $R^2$, $R^3$, and $R^4$ are chosen from alkyl groups, alkyl ether groups, acetyl groups, and $CF_3$ groups. Without intending to be bound by any particular theory, it is believed that substitution at these positions surprisingly increases the oxidation potential through a steric effect.

In other embodiments, one or more of the (D) electron donor compound has the following structure:

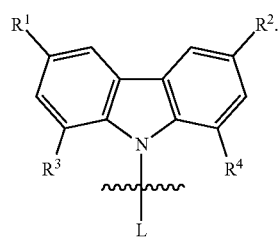

In these embodiments, X is the covalent bond such that the center ring is a five membered ring, as shown immediately above. In various embodiments, each of $R^1$, $R^2$, $R^3$, and $R^4$ is independently an alkyl group, a haloalkyl group (e.g. mono-, di-, or tri-halo), a perhaloalkyl group, an acyl group, an acyloxy group, an acetyl group, a haloacetyl group, an alkaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, a methylsulfonyloxyl group, a nitro group, an alkyl ether group, a trialkylammoniumalkyl group, a phosphate group, a phosphonate group, or an alkyl phosphonate group. In one embodiment, one of $R^3$ and $R^4$ is a hydrogen atom and the other of $R^3$ and $R^4$ is not a hydrogen atom. In another embodiment, each of $R^3$ and $R^4$ is a hydrogen atom.

In other embodiments, each of $R^1$ and $R^2$ is independently an alkyl group, a haloalkyl group (e.g. mono-, di-, or tri-halo), a perhaloalkyl group, an acyl group, an acyloxy group, an acetyl group, a haloacetyl group, an alkaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, a methylsulfonyloxyl group, a nitro group, an alkyl ether group, a trialkylammoniumalkyl group, a phosphate group, a phosphonate group, or an alkyl phosphonate group. In related embodiments, each of $R^3$ and $R^4$ is independently an alkyl group having 1 to 12 carbon atoms or a haloalkyl group (e.g. mono-, di-, or tri-halo) having 1 to 12 carbon atoms. Alternatively, one of $R^3$ and $R^4$ is a hydrogen atom. In one embodiment, one of $R^3$ and $R^4$ is a hydrogen atom whereas the other of $R^3$ and $R^4$ is not a hydrogen atom.

In further embodiments, each of $R^1$ and $R^2$ is independently an alkyl group having 1, 2, 3, 4, 5, or 6 carbon atoms or 1-12 carbon atoms, a trifluoromethyl group, a halo group, a cyano group, an alkyl ether group having 1-6 or 1-12 carbon atoms, or a trialkylammoniumalkyl group having 1-12 carbon atoms. In other embodiments, each of $R^3$ and $R^4$ are independently an alkyl group having 1, 2, 3, 4, 5, or 6 carbon atoms or 1-12 carbon atoms, a haloalkyl group (e.g.

mono-, di-, or tri-halo) having 1-6 or 1-12 carbon atoms, a perhaloalkyl group having 1-6 or 1-12 carbon atoms, an acyl group, or a haloacyl group. Alternatively, all values and ranges of values within those values described above are hereby expressly contemplated in various non-limiting embodiments.

In still other embodiments, each of $R^3$ and $R^4$ are sterically bulky. The terminology "sterically bulky" is appreciated by those of skill in the art. For example, each of $R^3$ and $R^4$ may be a $C_2$-$C_4$ alkyl group, such as an isopropyl, butyl, isobutyl, sec-butyl, or tert-butyl group. These types of groups may shift a potential to a more positive value without sacrificing (or at least minimizing an effect on) stability of the compound. However, and without intending to be bound by any particular theory, it is believed that the effect of bulky substituents is typically larger for phenothiazine than for carbazole. Alternatively, each of $R^3$ and $R^4$ may be a $C_2$-$C_5$ alkyl group and may include those groups described above and neopentyl groups. The identity of the groups attached to the nitrogen of the carbazole may be chosen to increase or decrease solubility, by one of skill in the art. In still other embodiments, each of $R^3$ and $R^4$ may be methyl and/or $CF_3$ groups. Alternatively, one of $R^3$ and $R^4$ is a hydrogen atom. In one embodiment, one of $R^3$ and $R^4$ is a hydrogen atom whereas the other of $R^3$ and $R^4$ is not a hydrogen atom.

In various embodiments, each of $R^1$ and $R^2$ is independently an alkyl group, a haloalkyl group (including perhaloalkyl), or an alkyl ether group and at least one of $R^3$ and $R^4$ is an alkyl group, a haloalkyl group (including perhaloalkyl), an alkyl ether group, an acyl group, or a haloacyl group. In other embodiments, each of $R^1$, $R^2$, $R^3$, and $R^4$ are chosen from alkyl groups, alkyl ether groups, acetyl groups, and $CF_3$ groups. Without intending to be bound by any particular theory, it is believed that substitution at these positions surprisingly increases the oxidation potential through a steric effect.

In other embodiments, one or more of the (D) electron donor compound has the following structure:

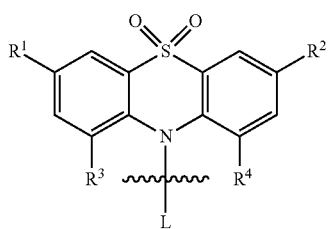

In various embodiments, $R^1$ and $R^2$ are independently an alkyl group, a nitrile group, a haloalkyl group, a perhaloalkyl group, an acyl group, and acyloxy group, an acetyl group, a haloacetyl group, an alkylaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, an arylhaloalkyl group, a methylsulfonyloxyl group, a nitro group, an alkyl ether group, a haloalkylether group, a trialkylammoniumalkyl group, a phosphate group, a phosphonate group, or an alkyl phosphonate group. $R^3$ and/or $R^4$ may independently hydrogen, an alkyl group, a haloalkyl group, a perhaloalkyl group, an acyl group, and acyloxy group, an acetyl group, a haloacetyl group, an alkylaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, an arylhaloalkyl group, a methylsulfonyloxyl group, a nitro group, an oxo group, an alkyl ether group, a haloalkylether group, a trialkylammoniumalkyl group, a phosphate group, a phosphonate group, or an alkyl phosphonate group.

In other embodiments, $R^1$ and $R^2$ are independently an alkyl group, a nitrile group, a haloalkyl group (e.g. mono-, di-, or tri-halo), a perhaloalkyl group, an acyl group, an acyloxy group, an acetyl group, a haloacetyl group, an alkaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, a methylsulfonyloxyl group, a nitro group, an alkyl ether group, a trialkylammoniumalkyl group, a phosphate group, a phosphonate group, or an alkyl phosphonate group. In one embodiment, one or both of $R^3$ and $R^4$ is hydrogen. In another embodiment, one of $R^3$ and $R^4$ is a hydrogen atom, whereas the other of $R^3$ and $R^4$ is not a hydrogen atom. In other embodiments, $R^3$ is an alkyl group having 1, 2, 3, 4, 5, or 6 carbon atoms or 1-12 carbon atoms, a haloalkyl group (e.g. mono-, di-, or tri-halo) having 1-6 or 1-12 carbon atoms, a perhaloalkyl group having 1-6 or 1-12 carbon atoms, an alkyl ether group having 1-6 or 1-12 carbon atoms, or a trialkylammoniumalkyl group having 1-6 or 1-12 carbon atoms. Alternatively, all values and ranges of values within those values described above are hereby expressly contemplated in various non-limiting embodiments.

In further embodiments, $R^1$ and $R^2$ are independently an alkyl group having 1, 2, 3, 4, 5, or 6 carbon atoms or 1-12 carbon atoms, a trifluoromethyl group, a halo group, a cyano group, an alkyl ether group having 1 to 12 carbon atoms, an alkyl ether group having 1-12 carbon atoms, or a trialkylammoniumalkyl group having 1 to 12 carbon atoms. In other embodiments, $R^3$ and $R^4$ are independently an alkyl group having 1, 2, 3, 4, 5, or 6 carbon atoms or 1-12 carbon atoms, a haloalkyl group (e.g. mono-, di-, or tri-halo) having 1-6 or 1-12 carbon atoms, a perhaloalkyl group having 1-6 or 1-12 carbon atoms, an acyl group, a haloacyl group, or a perhaloacyl group. Non-limiting examples of suitable alkyl groups are methyl, ethyl, propyl, isopropyl, butyl, isobutyl, sec-butyl, tert-butyl, neopentyl, n-pentyl, hexyl, octyl, and the like, as appreciated by those of skill in the art. Alternatively, all values and ranges of values within those values described above are hereby expressly contemplated in various non-limiting embodiments.

In still other embodiments, one of $R^3$ and $R^4$ is sterically bulky. In another embodiment, each of $R^3$ and $R^4$ is sterically bulky. The terminology "sterically bulky" is appreciated by those of skill in the art. For example, one or each of $R^3$ and $R^4$ may be $C_2$-$C_4$ alkyl group, such as an isopropyl, butyl, isobutyl, sec-butyl, or tert-butyl group. These types of groups may shift a potential to a more positive value without sacrificing (or at least minimizing an effect on) stability of the compound. In some instances, these types of groups may actually enhance stability of the compound. Alternatively, one or each of $R^3$ and $R^4$ may be a $C_2$-$C_5$ alkyl group and may include those groups described above and neopentyl groups. In still other embodiments, each of $R^3$ and $R^4$ may be methyl and/or $CF_3$ groups.

In various embodiments, $R^1$ and $R^2$ are independently an alkyl group, a haloalkyl group (including perhaloalkyl), or an alkyl ether group and at least one of $R^3$, $R^3$, and $R^4$ is an alkyl group, a haloalkyl group (including perhaloalkyl), an alkyl ether group, an acyl group, or a haloacyl group. In other embodiments, each of $R^1$, $R^2$, $R^3$, and $R^4$ are chosen from alkyl groups, alkyl ether groups, acetyl groups, and $CF_3$ groups. Without intending to be bound by any particular theory, it is believed that substitution at some of these positions (such as, e.g., at $R^3$ and/or $R^4$) surprisingly increases the oxidation potential through a steric effect.

In one particular embodiment, $R^1$ and $R^2$ are independently an alkyl group or a nitrile group. In another embodiment, $R^3$ is an alkyl group, a haloalkyl group, a perhaloalkyl group, an acyl group, and acyloxy group, an acetyl group, a haloacetyl group, an alkylaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, an arylhaloalkyl group, a methylsulfonyloxyl group, a nitro group, an oxo group, an alkyl ether group, a haloalkylether group, a trialkylammoniumalkyl group, a phosphate group, a phosphonate group, an alkyl phosphonate group, or a trialkylanilinium group. In various embodiments, one or both of $R^3$ and $R^4$ are independently hydrogen, an alkyl group, a haloalkyl group, a perhaloalkyl group, an acyl group, and acyloxy group, an acetyl group, a haloacetyl group, an alkylaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, an arylhaloalkyl group, a methylsulfonyloxyl group, a nitro group, an alkyl ether group, a haloalkylether group, a trialkylammoniumalkyl group, a phosphate group, a phosphonate group, or an alkyl phosphonate group.

In an additional embodiment, one or more of the (D) electron donor compound has the following structure:

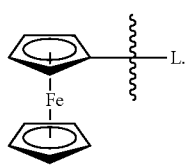

(D2)

This structure (D2) may be utilized along with any of the donor structures (D) above or independently from the other donor structures (D).

Additionally, it is noted that L in each of the structures above is the linker.

Linker (L):

Referring now to the linker (L), each L may be a linking compound chosen from an alkyl group having 2 to 6 carbon atoms, an aromatic group, and a direct bond between the electron donor compound (D) and the electron acceptor compound (A). In various embodiments, the alkyl group has 2, 3, 4, 5, or 6 carbon atoms and may be linear, branched, or cyclic. In one embodiment, (L) is —$CH_2$—$CH_2$—$CH_2$—. In another embodiment, (L) is phenyl or phenylene. The aromatic group may be any known in the art, e.g. an aryl or substituted aryl group. In various embodiments, each (L) may also include an ether, an ammonium group, or a phosphonium group. In embodiments where the linker (L) is a direct bond, the electron donor compound (D) is directly bonded to the electron acceptor compound (A) such as, for example, with a covalent bond.

Electron Acceptor Compound (A):

Referring back, and in an embodiment, one or more of the (A) electron acceptor compound may have the following structure (A1) or (A2) or (A3) or (A4) or (A5):

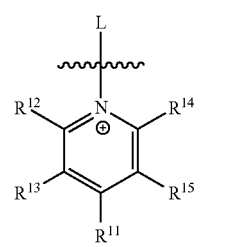

(A1)

or

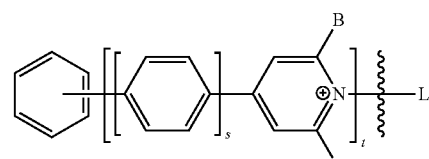

(A2)

or

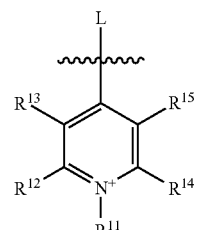

(A3)

or

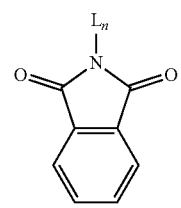

(A4)

or

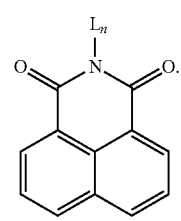

(A5)

Relative to (A1) and (A3), each of $R^{12}$ and $R^{14}$ is a phenyl group, a hydrogen atom, a aryl group or a substituted aryl group, or an alkyl group having 1 to 6 carbon atoms, and each of $R^{13}$ and $R^{15}$ is a hydrogen atom or an alkyl group having 1 to 6 carbon atoms. In various embodiments, each alkyl group independently has 2, 3, 4, 5, or 6 carbon atoms and may be linear, branched, or cyclic.

Relative to (A1) and (A3), $R^{11}$ is chosen from a hydrogen atom, an alkyl group, an acetyl group, an aryl group, a substituted aryl group, or a group having the following structure (P1) or (P2):

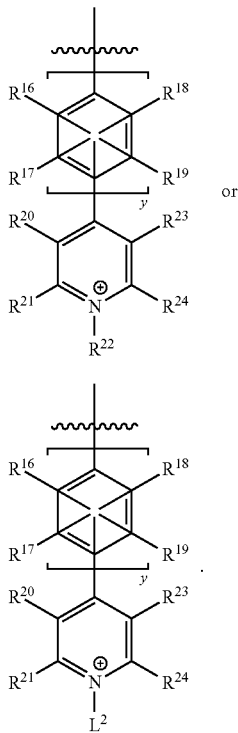

(P1)

(P2)

For (A3), $R^{11}$ is any of the aforementioned groups except for a hydrogen atom.

The aforementioned alkyl group of $R^{11}$ may be any known in the art and may be linear, branched, or cyclic. In various embodiments, the alkyl group has 1 to 6 carbon atoms, e.g. 2, 3, 4, 5, or 6 carbon atoms. In other various embodiments, the alkyl group may be an alkyl group, an alkyl ether group, an alkyl oligoether group, a trialkylammonium alkyl group, an alkyl phosphate group, an alkyl phosphonate group, or an alkyl phosphonium group. Similarly, the position of nitrogen may also be anywhere on the ring, e.g. ortho, meta, or para, relative to the optional phenyl middle unit of y subunits. The substituted aryl group may be any as described herein.

Moreover, relative to (P1) and (P2), y is a number from 0 to 4, e.g. 0, 1, 2, 3, or 4. Moreover, each of $R^{16}$-$R^{19}$ is a phenyl group, a hydrogen atom, or an alkyl group having 1 to 6 carbon atoms. In various embodiments, each alkyl group independently has 1, 2, 3, 4, 5, or 6 carbon atoms and may be linear, branched, or cyclic. Additionally, any of $R^{16}$-$R^{19}$ may be at any point on the ring.

Additionally, for (A1) and (A2), each of $R^{20}$, $R^{21}$, $R^{23}$, and $R^{24}$ is a phenyl group, a hydrogen atom, or an alkyl group having 1 to 6 carbon atoms. $R^{22}$ is a phenyl group or an alkyl group having 1 to 6 carbon atoms. In various embodiments, each alkyl group independently has 1, 2, 3, 4, 5, or 6 carbon atoms and may be linear, branched, or cyclic. Additionally, wherein $L^2$ is optionally a second or additional linker if z is 1 to 5, e.g. 1, 2, 3, 4, or 5. However, $L^2$ need not be utilized.

While (P1) and (P2) allow for attachment at the tail, it should be appreciated that (P1) and (P2) could allow for attachment at any position of the structure. Additionally, (A1) allows for attachment at the head and (A3) allows for attachment at the tail. It should be appreciated that (A1) and (A3) could allow for attachment at any position of the structures.

Referring back, and relative to (A2), s is a number from 0 to 2, e.g. 0, 1, or 2, t is a number from 1 to 6, e.g. 1, 2, 3, 4, 5, or 6, and each B is a hydrogen atom, an alkyl group having 1 to 6 carbon atoms, or an aryl or substituted aryl group. Again, in various embodiments, each alkyl group independently can have 1, 2, 3, 4, 5, or 6 carbon atoms and may be linear, branched, or cyclic. Non-limiting examples of aryl groups are phenyl groups. Non-limiting examples of substituted aryl groups are 4-methylphenyl, 4-methoxyphenyl, 4-(t-butyl)phenyl, 2,4-dimethylphenyl, 2,4,6-trimethylphenyl, and the like. In various embodiments, typical positions are 4, then 2 and/or 6. However, substitution could be on all rings of (A2). Additionally, the pyridine could also be substituted at positions 3 and/or 5. In still other embodiments, the substituents are short alkyl groups ($C_1$-$C_4$) and/or short alkoxy groups ($C_1$-$C_4$).

In various embodiments, one or more of the electron acceptor compound (A) may be an alkyl-substituted version of any one of acceptor compounds (A1), (A2), and (A3) described above.

In another embodiment, electron acceptor compound (A2) is further defined as structure (A6) below:

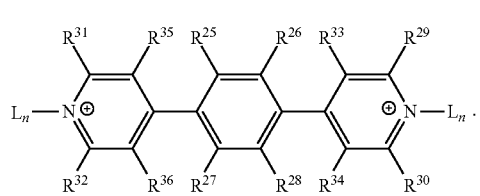

(A6)

Structure (A6) is an alkyl-substituted version of structure (A2). In structure (A6), $R^{25}$-$R^{36}$ may be the same or different and may be an alkyl group having from 1 to 4 carbon atoms, an alkyl ether group, an alkyl triammonium alkyl group, an oligoether group, a phenyl group, or hydrogen. In one embodiment, each of $R^{25}$ and $R^{28}$ is an alkyl group having from 1 to 4 carbon atoms, and each of the remaining $R^{26}$, $R^{27}$, and $R^{29}$-$R^{36}$ is a hydrogen atom. With this embodiment, it has been found that the reduced pyridines are unable to achieve coplanarity with the central bridging phenyl group, resulting in a more negative reduction potential. The lack of planarity may also promote solubility of the resultant neutral species upon reduction. In another embodiment, each of $R^{25}$, $R^{28}$, and $R^{29}$-$R^{36}$ groups is an alkyl group having from 1 to 4 carbon atoms and each of the remaining $R^{25}$-$R^{32}$ groups is a hydrogen atom. In another embodiment, each of $R^{25}$-$R^{28}$ groups is an alkyl group having from 1 to 4 carbon atoms and each of the remaining $R^{29}$-$R^{36}$ groups is a hydrogen atom. In still another embodiment, each of $R^{25}$-$R^{32}$ groups is an alkyl group having from 1 to 4 carbon atoms and the remaining $R^{33}$-$R^{36}$ groups is a hydrogen atom.

In an alternative embodiment, one or more of the electron acceptor compound (A) can be an aryl imide chosen from (A4) and (A5) above. These aryl imide compounds have low molecular weights, reasonable redox potentials, reversible electrochemistry, and relatively stable reduction products. Structure (A4) is pthalimide. In an embodiment, the electron acceptor compound having structure (A4) is further defined as pyromellitic diimide given by the structure (A7) below:

(A7)

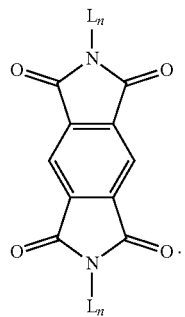

In another embodiment, the electron acceptor compound having structure (A5) is a rylene dye. In this embodiment, the electron acceptor compound having structure (A5) is further defined by structure (A8) or (A9):

(A8)

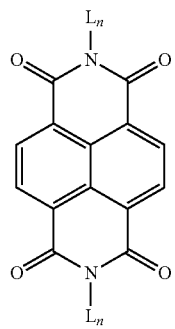

or (A9)

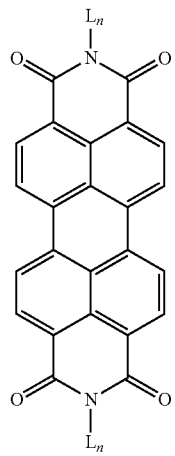

In alternative embodiments, the electron acceptor compound (A) can be a derivative of structure (A5) or (A8) or (A9) having substituents on any one or more of the aromatic ring positions to improve solubility. Non-limiting examples of substituents include an alkyl group, an alkyl ether or oligoether group, a trialkylammonium alkyl group, an alkyl phosphonate group, an alkyl phosphate group, an alkyl phosphonium group, an alkyl sulfonate group, and alkyl sulfate group, an alkyl carboxylate group, and a cyanoalkyl group. It is contemplated that one or more of the substituents could also be an aryl group.

Additional Embodiments

In various embodiments, the electron donor compound (D) is chosen from one of the compounds below:

(Donor 1)

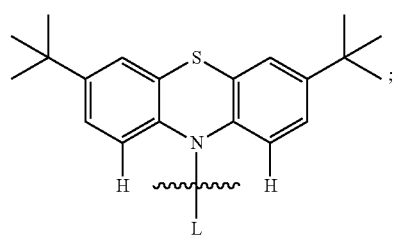

(Donor 2)

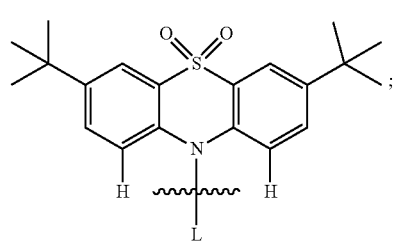

(Donor 3)

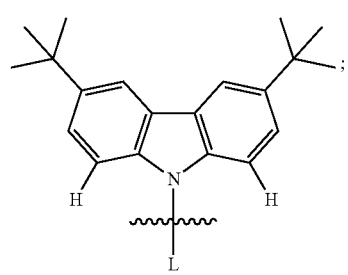

(Donor 4)

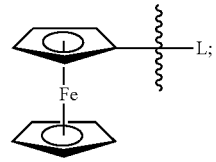

(Donor 5)

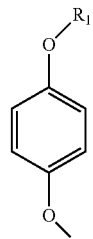

(Donor 6)

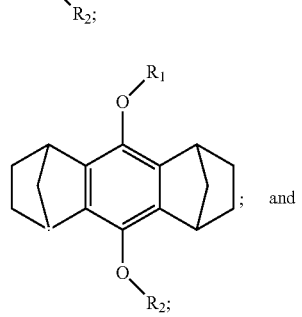

; and (Donor 7)

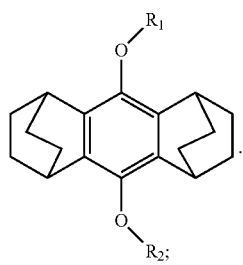

Relative to (Donor 1), X is S, each of $R^1$ and $R^2$ is t-butyl, and $R^3$, $R^4$, $R^7$, $R^8$, $R^9$, and $R^{10}$ are each hydrogen.

Relative to (Donor 2), X is $SO_2$, each of $R^1$ and $R^2$ is an alkyl having 1 to 4 carbon atoms, and $R^3$, $R^4$, $R^7$, $R^8$, $R^9$, and $R^{10}$ are each hydrogen.

Relative to (Donor 3), X is a covalent bond, each of $R^1$ and $R^2$ is t-butyl, and $R^3$, $R^4$, $R^7$, $R^8$, $R^9$, and $R^{10}$ are each hydrogen.

Relative to (Donor 5), (Donor 6), and (Donor 7), each of $R_1$ and $R_2$ is an alkyl group. Additionally, the attachment position may be at $R_1$ or $R_2$, such that $R_1$ or $R_2$ can be replaced with the (L) linker. For (Donor 5), (L) could also be attached to any one of the aromatic carbons.

In additional embodiments, the linker (L) is chosen from one of the linkers below:

(Linker 1)

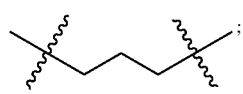

(Linker 2)

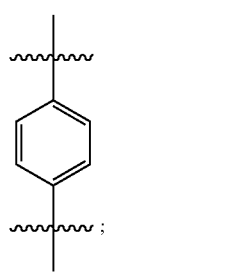

(Linker 3)

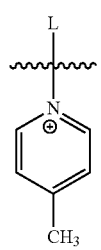; and (Linker 4)

Covalent Bond.

In still further embodiments, the electron acceptor compound (A) is chosen from one of the following compounds below:

(Acceptor 1)

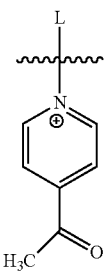

(Acceptor 2)

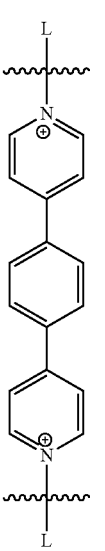

(Acceptor 3)

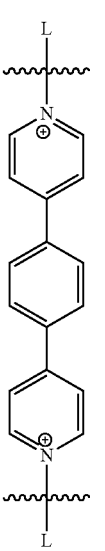

(Acceptor 4)

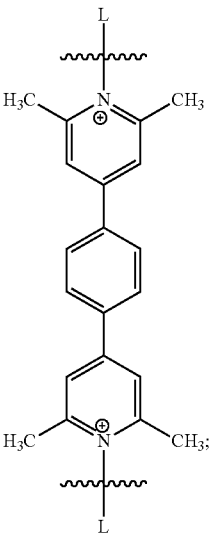

(Acceptor 5)

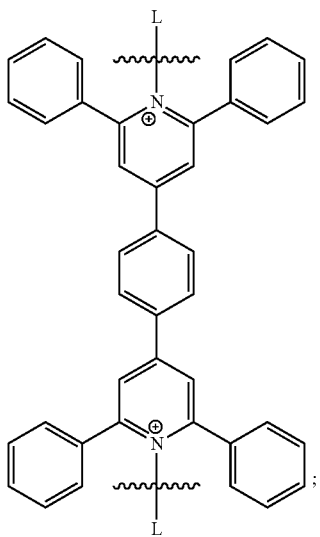

(Acceptor 6)

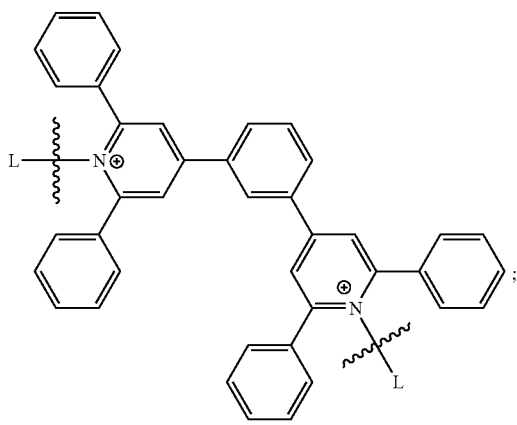

(Acceptor 7)

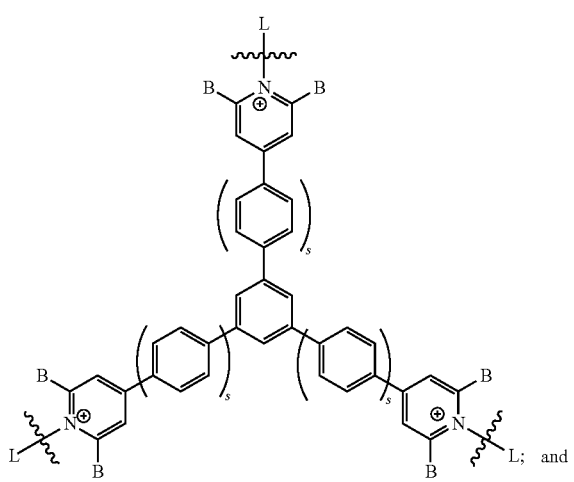

(Acceptor 8)

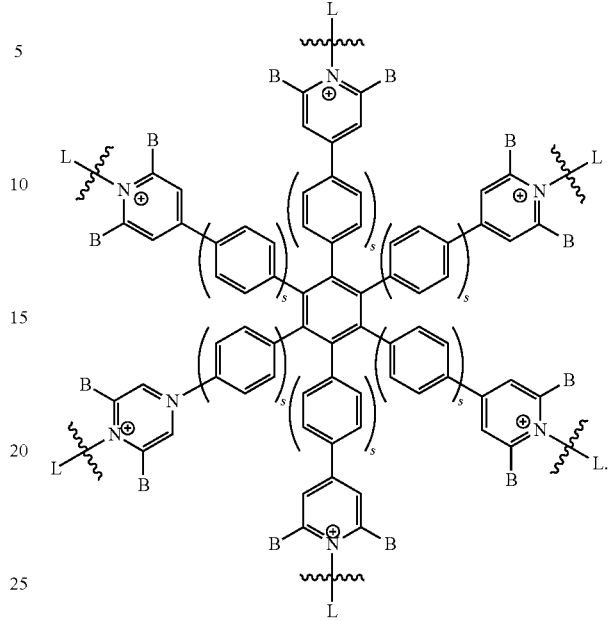

Relative to (Acceptor 1), structure (A1) is utilized wherein $R^{11}$ is a methyl group and each of $R^{12}$, $R^{13}$, $R^{14}$, and $R^{15}$ are hydrogen.

Relative to (Acceptor 2), structure (A1) is utilized wherein $R^{11}$ is an acetyl group and each of $R^{12}$, $R^{13}$, $R^{14}$, and $R^{15}$ are hydrogen.

Relative to (Acceptor 3), structure (A1) is utilized wherein $R^{11}$ is compound (P2), y is 1, and each of $R^{12}$, $R^{13}$, $R^{14}$, $R^{15}$, $R^{16}$, $R^{17}$, $R^{18}$, $R^{19}$, $R^{20}$, $R^{21}$, $R^{23}$, and $R^{24}$ are hydrogen.

Relative to (Acceptor 4), structure (A1) is utilized wherein $R^{11}$ is compound (P2), y is 1, each of $R^{13}$, $R^{15}$, $R^{16}$, $R^{17}$, $R^{18}$, $R^{19}$, $R^{20}$, and $R^{23}$ are hydrogen, and $R^{12}$, $R^{14}$, $R^{21}$, and $R^{24}$ are each methyl.

Relative to (Acceptor 5), structure (A1) is utilized wherein $R^{11}$ is compound (P2), y is 1, each of $R^{13}$, $R^{15}$, $R^{16}$, $R^{17}$, $R^{18}$, $R^{19}$, $R^{20}$, and $R^{23}$ are hydrogen, and $R^{12}$, $R^{14}$, $R^{21}$, and $R^{24}$ are each phenyl. Acceptor 5 has the pyridines linked in a para orientation (at C1 and C4 of the central benzene).

Relative to (Acceptor 6), structure (A1) is utilized wherein $R^{11}$ is compound (P2), y is 1, each of $R^{13}$, $R^{15}$, $R^{16}$, $R^{17}$, $R^{18}$, $R^{19}$, $R^{20}$, and $R^{23}$ are hydrogen, and $R^{12}$, $R^{14}$, $R^{21}$, and $R^{24}$ are each phenyl. Acceptor 6 has the pyridines linked in a meta arrangement (at C1 and C3).

Relative to (Acceptor 7), structure (A2) is utilized wherein each B is a hydrogen atom, an alkyl group having 1 to 6 carbon atoms, or an aryl or substituted aryl group, s is a number from 0 to 2, and t is 3.

Relative to (Acceptor 8), structure (A2) is utilized wherein each B is a hydrogen atom, an alkyl group having 1 to 6 carbon atoms, or an aryl or substituted aryl group, s is a number from 0 to 2, and t is 6.

Additional embodiments of electron acceptor compounds are set forth below:

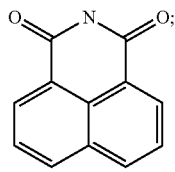
(Acceptor 9)

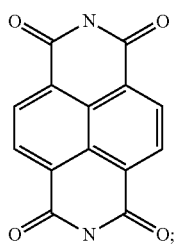
(Acceptor 10)

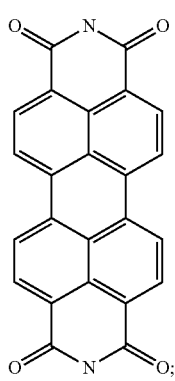
(Acceptor 11) and

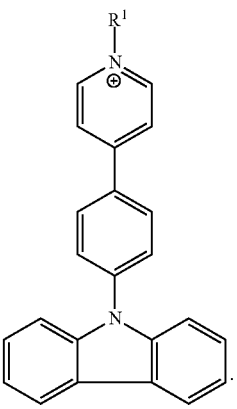
(Acceptor 12)

Notably, for any one or more of the aforementioned (A) electron acceptor compounds, only one point of linkage to (L) needs be present. In various embodiments of (A) wherein two or more points of linkage to (L) are shown, any one or more of these may be used as a linkage point to an (L) or may alternatively be a hydrogen atom or an alkyl group having 1, 2, 3, 4, 5, or 6, carbon atoms, that may be linear, branched, or cyclic. Additionally, for any one or more of the aforementioned (A) electron acceptor compounds the electron donor compound (D) may be linked to the nitrogen atom N of the pyridine through a linker (L). Alternatively, the electron donor compound (D) can be linked any of the aforementioned (A) electron acceptor compounds at positions other than the N of the pyridine, such as at the C-2 or C-4 positions through a linker (L). A non-limiting example of a structure where the donor compound (D) is linked to the C-4 of the pyridine of the acceptor compound (A) with a phenylene linker (L):

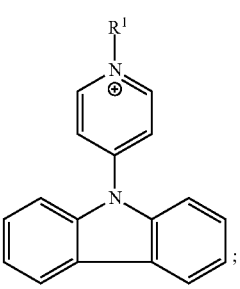
(Active Material 1)

In still other embodiments, the (A) electron acceptor compound may be as described as a 1 electron pyridinium-based acceptor. Examples are set forth in Physical Organic Approach to Persistent, Cyclable, Low-Potential Electrolytes for Flow Battery Applications; J. Am. Chem. Soc. 2017, 139, 2924-2927, which is expressly incorporated herein by reference in various non-limiting embodiments.

As previously mentioned, the linker (L) can be a direct bond (such as a covalent) between the donor compound (D) and the acceptor compound (A). Non-limiting examples of structures of the active material where the linker (L) is a covalent bond between the donor compound (D) and the acceptor compound (A) are set forth below:

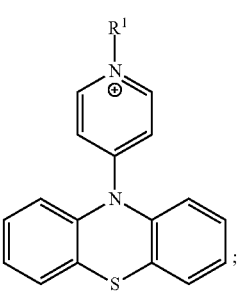
(Active Material 2)

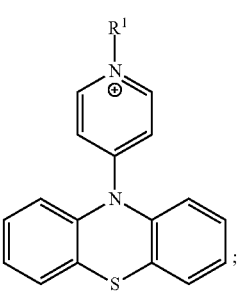
(Active Material 3)

(Active Material 4)

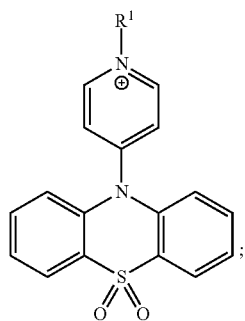

(Active Material 5)

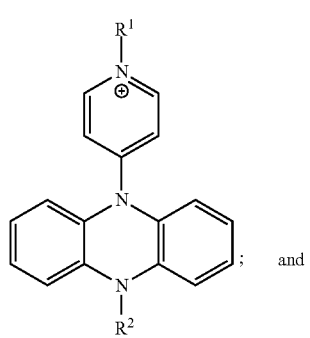

and (Active Material 6)

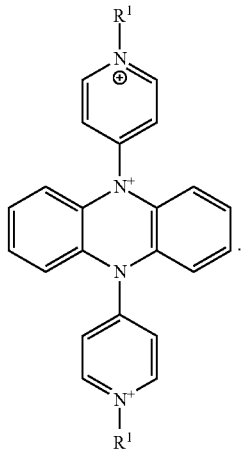

Relative to (Active Material 2) through (Active Material 6), $R^1$ and $R^2$ are independently a phenyl group, an aryl group or substituted aryl group, an alkyl group having 2 to 6 carbon atoms, an alkyl ether group, an alkyl oligoether group, a trialkylammonium alkyl group, an alkyl phosphate group, an alkyl phosphonate group, or an alkyl phosphonium group. In various embodiments, each alkyl group independently has 2, 3, 4, 5, or 6 carbon atoms and may be linear, branched, or cyclic.

Additional non-limiting examples of active material are shown below as (Active Material 7)-(Active Material 9):

(Active Material 7)

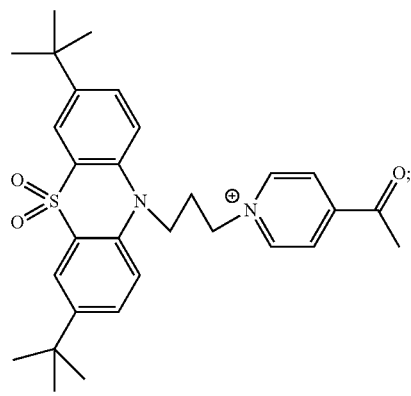

(Active Material 8)

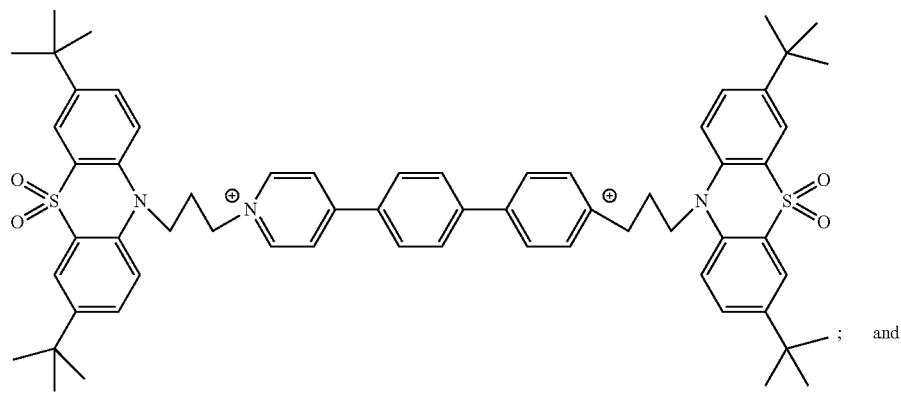

; and

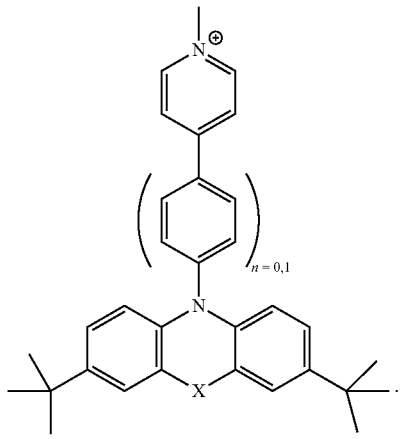

(Active Material 9)

In an embodiment, the structure of the active material can be designed to allow for different attachment points on the pyridine, such shown below:

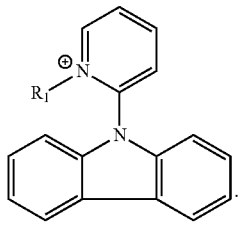

(Active Material 10)

Relative to (Active Material 10) above, $R^1$ is a phenyl group, an aryl group or substituted aryl group, an alkyl group having 2 to 6 carbon atoms, an alkyl ether group, an alkyl oligoether group, a trialkylammonium alkyl group, an alkyl phosphate group, an alkyl phosphonate group, or an alkyl phosphonium group. In various embodiments, each alkyl group independently has 2, 3, 4, 5, or 6 carbon atoms and may be linear, branched, or cyclic.

In yet another embodiment, the structure of the active material can be designed to allow for different attachment points on the donor compound, such as shown below:

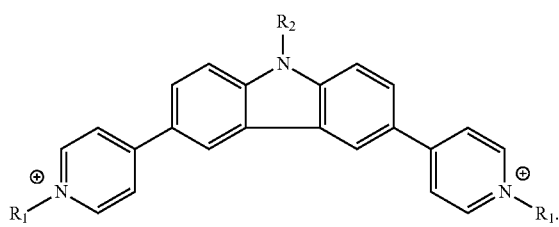

(Active Material 11)

Relative to (Active Material 11) above, $R^1$ and $R^2$ are independently a phenyl group, an aryl group or substituted aryl group (such as a trialkylammoniumphenyl group), an alkyl group, an alkyl ether group, an alkyl oligoether group, a trialkylammonium alkyl group, an alkyl phosphate group, an alkyl phosphonate group, or an alkyl phosphonium group.

In further embodiments of (F1) and (F2), (L) is —$CH_2$—$CH_2$—$CH_2$— or phenyl. In one embodiment, v is 0 and z is 0. In another embodiment, v is 1 and z is 1. In a further embodiment, v is 1 and x is 1. In yet another embodiment, y is 1 and x is 1, two (D) electron donor compounds are utilized wherein in each (D), X is $SO_2$, each of $R^1$ and $R^2$ is t-butyl, and $R^3$, $R^4$, $R^7$, $R^8$, $R^9$, and $R^{10}$ are each hydrogen, and wherein there is a single (A) electron acceptor compound wherein structure (A1) is utilized and wherein $R^{11}$ is compound (P2), y is 1, each of $R^{13}$, $R^{15}$, $R^{16}$, $R^{17}$, $R^{18}$, $R^{19}$, $R^{20}$, and $R^{23}$ are hydrogen, and $R^{12}$, $R^{14}$, $R^{21}$, and $R^{24}$ are each methyl.

In still another embodiment, y is 1 and x is 1, two (D) electron donor compounds are utilized wherein in each (D) X is a covalent bond, each of $R^1$ and $R^2$ is t-butyl, and $R^3$, $R^4$, $R^7$, $R^8$, $R^9$, and $R^{10}$ are each hydrogen, and wherein there is a single (A) electron acceptor compound wherein structure (A1) is utilized and wherein $R^{11}$ is compound (P2), y is 1, each of $R^{13}$, $R^{15}$, $R^{16}$, $R^{17}$, $R^{18}$, $R^{19}$, $R^{20}$, and $R^{23}$ are hydrogen, and $R^{12}$, $R^{14}$, $R^{21}$, and $R^{24}$ are each methyl.

In still another embodiment, this disclosure provides a redox flow battery that includes a cathode, an anode, a charge-carrying electrolyte, and an active material comprising two or more pyridine or substituted pyridine units, any two of which are separated by 1 to 3 phenyl or substituted phenyl groups, wherein one or more of the pyridine or substituted pyridine units are linked through a nitrogen atom to a moiety having a chemically reversible electrochemical oxidation. In this embodiment, the terminology "chemically reversible electrochemical oxidation" is used here to describe the observed response in a cyclic voltammetry experiment. Specifically, when the experiment is performed in propylene carbonate containing at least 0.1 M of an appropriate supporting electrolyte salt, the anodic and cathodic waves corresponding to the electrochemical oxidation process are identical or nearly identical in both height and area when measured at a sweep rate of 100 mV/s.

EXAMPLES

Various non-limiting examples of redox-flow batteries are formed and evaluated to determine a series of electrical properties set forth in Table 1 below. All electrochemical data is gathered using normal laboratory measurements-cyclic voltammetry and differential pulse voltammetry. Notably, the reference electrode used was a silver wire pseudoreference electrode and is susceptible to drift. While this may affect certain potential measurements, the overall redox flow battery cell voltage is expressed as the difference between the oxidation and reduction potential, and is not affected by the reference electrode drift.

TABLE 1

| Example | Active Material | $E_2Red$ | $E_1Red$ | $E_1Ox$ | $E_2Ox$ | Cell Voltage |
|---|---|---|---|---|---|---|
| 1 | D1-L1-A1 | — | −1.32(irr) | 0.75 | — | 2.07 |
| 2 | D2-L1-A1 | — | −1.53(irr) | 1.47 | — | 3.0 |
| 3 | D1-L1-A2 | −1.18 | −0.60 | 0.75 | 1.37 | 1.35, 2.55 |
| 4 | D2-L1-A2 | −1.45 | −0.82 | 1.32 | — | 2.14 |
| 5 | D3-L1-A2 | — | −0.62 | 1.23 | — | 1.85 |
| 6 | D5-L3-A2 | — | −0.72 | 1.34 | — | 2.06 |
| 7 | D1-L1-A3-L1-D1 | — | −0.86 | 0.64 | 1.26 | 1.50, 2.12 |
| 8 | D2-L1-A3-L1-D2 | — | −0.90(2e−) | 1.48(2e−) | — | 2.38 |
| 9 | D3-L1-A3-L1-D3 | — | 0.95(2e−) | 1.07(2e−) | — | 2.02 |
| 10 | D5-L3-A3-L3-D5 | — | 0.95(2e−) | 1.28(2e−) | — | 2.23 |
| 11 | D1-L3-A5-L3-D1 | — | −0.58(2e−) | 0.82(2e−) | — | 1.40 |
| 12 | D2-L3-A5-L3-D2 | — | −0.66(2e−) | 1.56(2e−) | — | 2.22 |
| 13 | D3-L2-A5-L2-D3 | −1.35(2e−) | −0.60, −0.69 | 1.30(2e−) | — | ca.1.95 |
| 14 | D4-L2-A5-L2-D4 | −1.74(2e−) | −1.05(2e−) | 0.22(2e−) | — | 1.27 |
| 15 | D4-L2-A6-L2-D4 | — | −1.23(4e) | 0.22(2e) | — | ca.1.45 |
| 16 | D1-L1-A9 | — | −1.38 | 0.51 | — | 1.89 |
| 17 | D2-L1-A9 | — | −1.29 | 1.35 | — | 2.70 |
| 18 | D3-L1-A9 | — | −1.14 | 1.24 | — | 2.39 |
| 19 | D1-L3-A10-L1-D1 | −0.99 | −0.58 | 0.63 | — | 1.21, 1.62 |
| 20 | D3-L1-A10-L1-D3 | −0.91 | −0.55 | 1.17(2e−) | — | 1.72, 2.08 |
| 21 | D1-L3-A12-L3-D1 | −1.47 | −0.927 | 0.58(2e−) | — | 1.52, 2.11 |
| 22 | D2-L4-(N-Mepy) | — | −1.41 | 1.48 | — | 2.89 |

D1 is Donor 1. D2 is Donor 2. D3 is Donor 3. D4 is Donor 4. Each is set forth above. D5 is represented by the following structure:

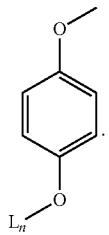

(D5)

L1 is Linker 1. L2 is Linker 2. L3 is Linker 3. L4 is Linker 4. Each is set forth above.

A1 is Acceptor 1. A2 is Acceptor 2. A3 is Acceptor 3. A5 is Acceptor 5. A6 is Acceptor 6. A7 is Acceptor 7. A9 is Acceptor 9. A10 is Acceptor 10. A12 is Acceptor 12. Each is set forth above.

N-Mepy is 4-(N-methylpyridinium).

$E_2Red$ refers to the reduction potential corresponding to the second reduction of the Active Material.

$E_1Red$ refers to the reduction potential corresponding to the first reduction of the Active Material.

$E_1Ox$ refers to the oxidation potential corresponding to the first oxidation of the Active Material.

$E_2Ox$ refers to the oxidation potential corresponding to the second oxidation of the Active Material.

The notation "irr" refers to a chemically irreversible electrochemical process.

The results above for these examples demonstrate that linked donor-acceptor compounds possessing suitable properties for use in a redox flow battery as described herein can be prepared. This table contains multiple examples of linked compounds showing well-separated (by >1 V) oxidation and reduction processes.

All combinations of the aforementioned embodiments throughout the entire disclosure are hereby expressly contemplated in one or more non-limiting embodiments even if such a disclosure is not described verbatim in a single paragraph or section above. In other words, an expressly contemplated embodiment may include any one or more elements described above selected and combined from any portion of the disclosure.

One or more of the values described above may vary by ±5%, ±10%, ±15%, ±20%, ±25%, etc. Unexpected results may be obtained from each member of a Markush group independent from all other members. Each member may be relied upon individually and or in combination and provides adequate support for specific embodiments within the scope of the appended claims. The subject matter of all combinations of independent and dependent claims, both singly and multiply dependent, is herein expressly contemplated. The disclosure is illustrative including words of description rather than of limitation. Many modifications and variations of the present disclosure are possible in light of the above teachings, and the disclosure may be practiced otherwise than as specifically described herein.

It is also to be understood that any ranges and subranges relied upon in describing various embodiments of the present disclosure independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present disclosure, and such ranges and subranges may be further delineated into relevant halves, thirds, quarters, fifths, and so on. As just one example, a range "of from 0.1 to 0.9" may be further delineated into a lower third, i.e. from 0.1 to 0.3, a middle third, i.e. from 0.4 to 0.6, and an upper third, i.e. from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

What is claimed is:

1. A redox flow battery comprising:
   (I) a cathode;
   (II) an anode;
   (III) a charge-carrying electrolyte; and
   (IV) an (a) oxidized and a (b) reduced form of an active material having the following formula:

  (F1) or

  (F2)

wherein each D is covalently bonded to an L, wherein each L is covalently bonded to an A, wherein x is a number from 0 to 5, v is a number from 0 to 5 and z is 0 or 1, wherein D is an electron donor compound, L is a linker, and A is an electron acceptor compound, wherein each D has the following structure (D1):

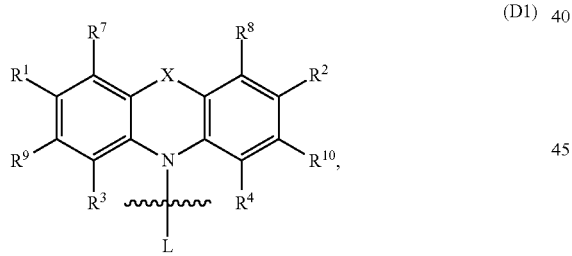 (D1)

wherein X is a covalent bond, a sulfur atom (S), $SO_2$, or $N-R^6$, and wherein each of $R^1, R^2, R^3, R^4, R^6, R^7, R^8, R^9$ and $R^{10}$ is independently a hydrogen atom, an alkyl group, a nitrile group, a haloalkyl group, a perhaloalkyl group, an acyl group, and acyloxy group, an acetyl group, a haloacetyl group, an alkylaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, an arylhaloalkyl group, a methylsulfonyloxyl group, a nitro group, an alkyl ether group, a haloalkylether group, a trialkylammoniumalkyl group, a phosphate group, a phosphonate group, or an alkyl phosphonate group;

wherein each L is chosen from an alkyl group having 2 to 6 carbon atoms, an aromatic group, and a covalent bond, and wherein each A has the following structure (A1) or (A2) or (A3) or (A4) or (A5):

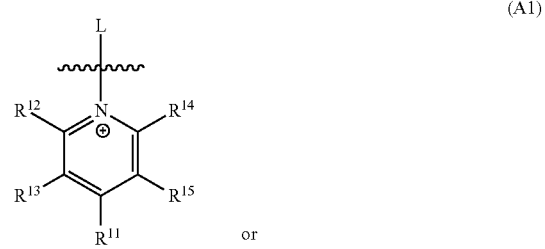 (A1)

or

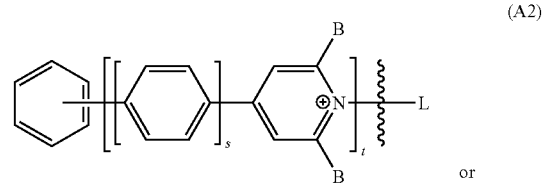 (A2)

or

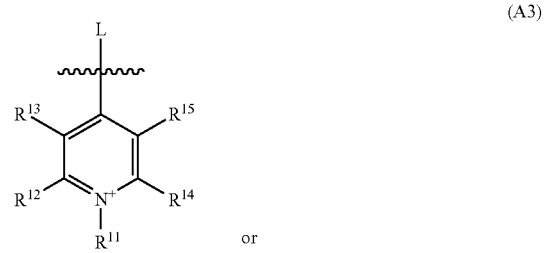 (A3)

or

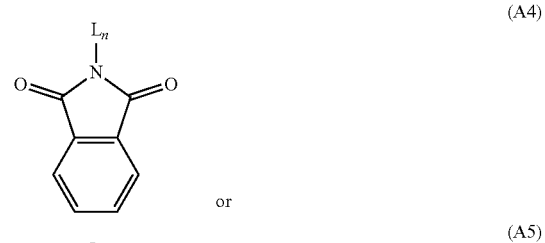 (A4)

or

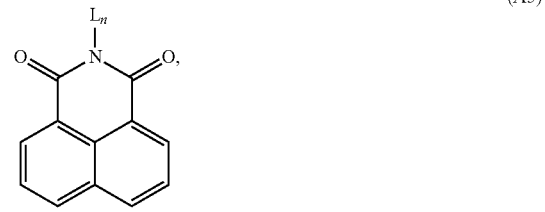 (A5)

wherein for each of (A1), (A2), and (A3):
   each of $R^{12}$ and $R^{14}$ is a phenyl group, a hydrogen atom, or an alkyl group having 1 to 6 carbon atoms, and each of $R^{13}$ and $R^{15}$ is a hydrogen atom or an alkyl group having 1 to 6 carbon atoms; and $R^{11}$ is chosen from a hydrogen atom, an alkyl group, an acetyl group, an aryl group, a substituted aryl group, or a group having the following structure (P1) or (P2):

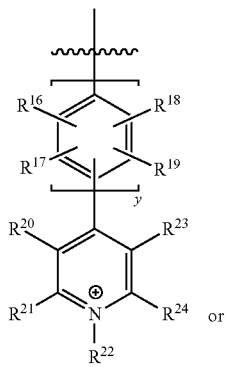

(P1)

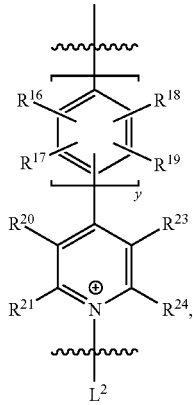

(P2)

wherein y is a number from 0 to 4; wherein each of $R^{16}$-$R^{19}$ is a phenyl group, a hydrogen atom, or an alkyl group having 2 to 6 carbon atoms; wherein each of $R^{21}$, $R^{22}$, and $R^{24}$ is a phenyl group, a hydrogen atom, or an alkyl group having 1 to 6 carbon atoms, wherein each of $R^{20}$ and $R^{23}$ is a hydrogen atom or an alkyl group having 1 to 6 carbon atoms; and wherein $L^2$ is optionally a second linker, and wherein in (A2) s is a number from 0 to 2, t is a number from 1 to 6, and each B is a hydrogen atom, an alkyl group having 1 to 6 carbon atoms, or an aryl or substituted aryl group.

2. The redox flow battery of claim 1 that is free of an ion-selective membrane separating said anode and said cathode to keep reduced catholyte and oxidized anolyte from mixing.

3. The redox flow battery of claim 1 wherein X is S, each of $R^1$ and $R^2$ is an alkyl having 1 to 4 carbon atoms, and $R^3$, $R^4$, $R^7$, $R^8$, $R^9$, and $R^{10}$ are each hydrogen.

4. The redox flow battery of claim 1 wherein X is $SO_2$, each of $R^1$ and $R^2$ is t-butyl, and $R^3$, $R^4$, $R^7$, $R^8$, $R^9$, and $R^{10}$ are each hydrogen.

5. The redox flow battery of claim 1 wherein X is a covalent bond, each of $R^1$ and $R^2$ is t-butyl, and $R^3$, $R^4$, $R^7$, $R^8$, $R^9$, and $R^{10}$ are each hydrogen.

6. The redox flow battery of claim 1 wherein structure (D1) is further defined as structure (Donor 1):

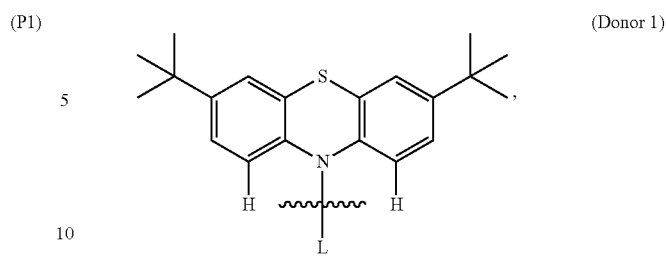

(Donor 1)

wherein L is the linker.

7. The redox flow battery of claim 1 wherein structure (D1) is further defined as structure (Donor 2):

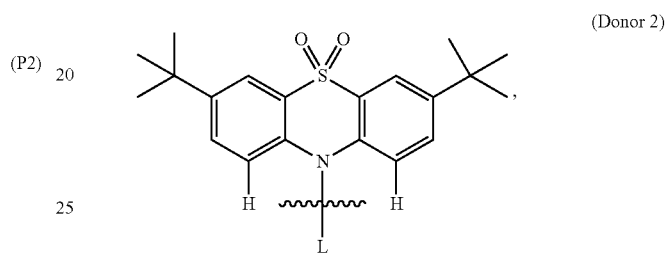

(Donor 2)

wherein L is the linker.

8. The redox flow battery of claim 1 wherein structure (D1) is further defined as structure (Donor 3):

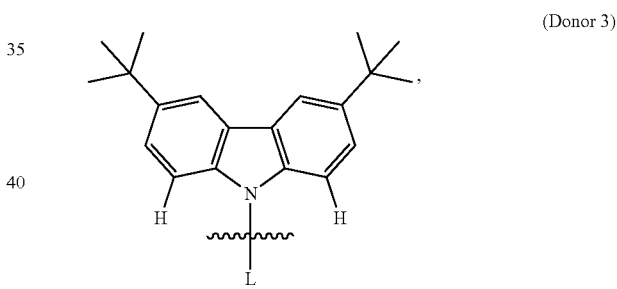

(Donor 3)

wherein L is the linker.

9. The redox flow battery of claim 1 wherein (L) is —$CH_2$—$CH_2$—$CH_2$—.

10. The redox flow battery of claim 1 wherein (L) is phenyl.

11. The redox flow battery of claim 1 wherein structure (A1) is utilized, wherein $R^{11}$ is compound (P2), y is 1, and each of $R^{12}$, $R^{13}$, $R^{14}$, $R^{15}$, $R^{16}$, $R^{17}$, $R^{18}$, $R^{19}$, $R^{20}$, $R^{21}$, $R^{23}$, and $R^{24}$ are hydrogen.

12. The redox flow battery of claim 1 wherein structure (A1) is utilized, wherein $R^{11}$ is compound (P2), y is 1, each of $R^{13}$, $R^{15}$, $R^{16}$, $R^{17}$, $R^{18}$, $R^{19}$, $R^{20}$, and $R^{23}$ are hydrogen, and $R^{12}$, $R^{14}$, $R^{21}$, and $R^{24}$ are each methyl.

13. The redox flow battery of claim 1 wherein structure (A1) is utilized, wherein $R^{11}$ is compound (P2), y is 1, each of $R^{13}$, $R^{15}$, $R^{16}$, $R^{17}$, $R^{18}$, $R^{19}$, $R^{20}$, and $R^{23}$ are hydrogen, and $R^{12}$, $R^{14}$, $R^{21}$, and $R^{24}$ are each phenyl.

14. The redox flow battery of claim 1 wherein v is 0 and z is 0.

15. The redox flow battery of claim 1 wherein v is 1 and z is 1.

16. The redox flow battery of claim 1 wherein v is 1 and x is 1.

17. The redox flow battery of claim 1 wherein structure (A2) is further defined as structure (A6):

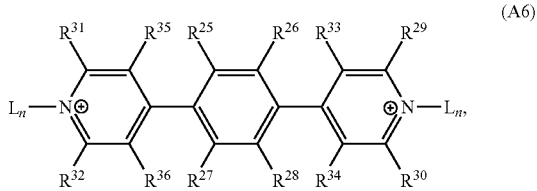

(A6)

wherein in (A6) $R^{25}$-$R^{36}$ is chosen from an alkyl group having from 1 to 4 carbon atoms, an alkyl ether group, an alkylammonium alkyl group, an oligoether group, a phenyl group, and hydrogen.

18. The redox flow battery of claim 17 wherein each of $R^{25}$-$R^{36}$ is hydrogen.

19. The redox flow battery of claim 1 wherein y is 1 and x is 1, wherein there are two (D) electron donor compounds wherein in each (D) X is $SO_2$, each of $R^1$ and $R^2$ is t-butyl, and $R^3$, $R^4$, $R^7$, $R^8$, $R^9$, and $R^{10}$ are each hydrogen, and wherein there is a single (A) electron acceptor compound wherein structure (A1) is utilized and wherein $R^{11}$ is compound (P2), y is 1, each of $R^{13}$, $R^{15}$, $R^{16}$, $R^{17}$, $R^{18}$, $R^{19}$, $R^{20}$, and $R^{23}$ are hydrogen, and $R^{12}$, $R^{14}$, $R^{21}$, and $R^{24}$ are each methyl.

20. The redox flow battery of claim 1 wherein y is 1 and x is 1, wherein there are two (D) electron donor compounds wherein in each (D) X is a covalent bond, each of $R^1$ and $R^2$ is t-butyl, and $R^3$, $R^4$, $R^7$, $R^8$, $R^9$, and $R^{10}$ are each hydrogen, and wherein there is a single (A) electron acceptor compound wherein structure (A1) is utilized and wherein $R^{11}$ is compound (P2), y is 1, each of $R^{13}$, $R^{15}$, $R^{16}$, $R^{17}$, $R^{18}$, $R^{19}$, $R^{20}$, and $R^{23}$ are hydrogen, and $R^{12}$, $R^{14}$, $R^{21}$, and $R^{24}$ are each methyl.

21. A redox flow battery comprising:
   (I) a cathode;
   (II) an anode;
   (III) a charge-carrying electrolyte; and
   (IV) an active material comprising two or more pyridine or substituted pyridine units, any two of which are separated by 1 to 3 phenyl or substituted phenyl groups, wherein one or more of the pyridine or substituted pyridine units are linked through a nitrogen atom to a moiety having a reversible electrochemical oxidation.

22. An active material for a redox flow battery with the active material having the following formula:

$$(D)-(L)-(A)-[(L)-(A)]_v-D_Z \quad (F1)$$

or $$(D)-(L)-(A)-(L-D)_X \quad (F2)$$

wherein each D is covalently bonded to an L, wherein each L is covalently bonded to an A, wherein x is a number from 0 to 5, v is a number from 0 to 5 and z is 0 or 1, wherein D is an electron donor compound, L is a linker, and A is an electron acceptor compound, wherein each D has the following structure (D1):

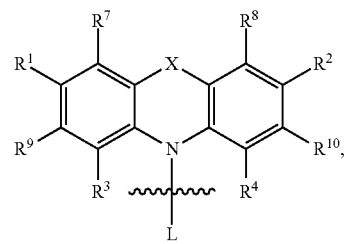

(D1)

wherein X is a covalent bond, a sulfur atom (S), $SO_2$, or N—$R^6$, and wherein each of $R^1$, $R^2$, $R^3$, $R^4$, $R^6$, $R^7$, $R^8$, $R^9$ and $R^{10}$ is independently a hydrogen atom, an alkyl group, a nitrile group, a haloalkyl group, a perhaloalkyl group, an acyl group, and acyloxy group, an acetyl group, a haloacetyl group, an alkylaryl group, an alkoxy group, an acetamido group, an amido group, an aryl group, an aralkyl group, an alkyl carboxyl group, an aryl carboxyl group, an alkylsulfonyl group, a benzoyl group, a carbamoyl group, a carboxy group, a cyano group, a formyl group, a halo group, a haloacetamido group, a haloacyl group, a haloalkylsulfonyl group, a haloaryl group, an arylhaloalkyl group, a methylsulfonyloxyl group, a nitro group, an alkyl ether group, a haloalkylether group, a trialkylammoniumalkyl group, a phosphate group, a phosphonate group, or an alkyl phosphonate group;

wherein each L is chosen from an alkyl group having 2 to 6 carbon atoms, an aromatic group, and a direct bond, and wherein each A has the following structure (A1) or (A2) or (A3) or (A4) or (A5):

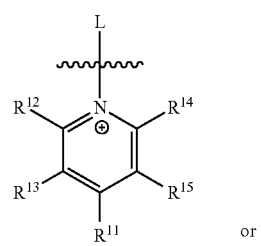

(A1)

or

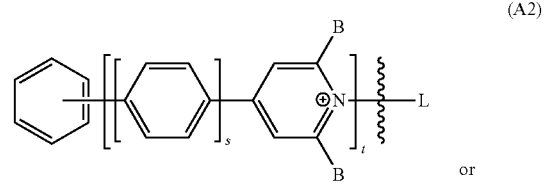

(A2)

or

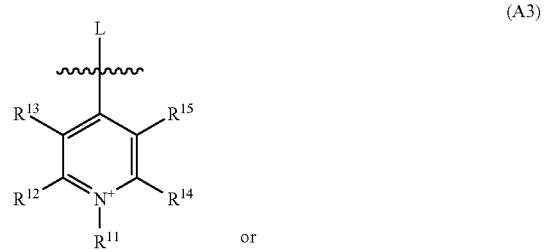

(A3)

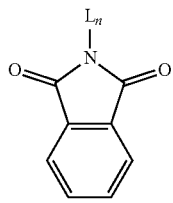

or

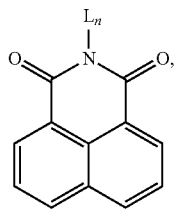

wherein for each of (A1), (A2), and (A3):

each of $R^{12}$ and $R^{14}$ is a phenyl group, a hydrogen atom, or an alkyl group having 1 to 6 carbon atoms, and each of $R^{13}$ and $R^{15}$ is a hydrogen atom or an alkyl group having 1 to 6 carbon atoms; and $R^{11}$ is chosen from a hydrogen atom, an alkyl group, an acetyl group, an aryl group, a substituted aryl group, or a group having the following structure (P1) or (P2):

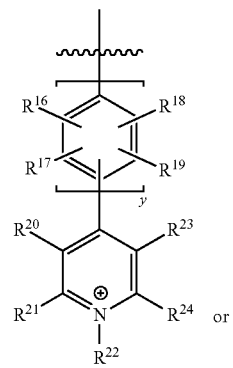

(P1)

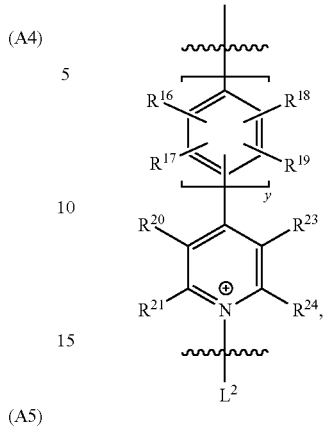

(P2)

wherein y is a number from 0 to 4; wherein each of $R^{16}$-$R^{19}$ is a phenyl group, a hydrogen atom, or an alkyl group having 1 to 6 carbon atoms; wherein each of $R^{21}$, $R^{22}$, and $R^{24}$ is a phenyl group, a hydrogen atom, or an alkyl group having 1 to 6 carbon atoms, wherein each of $R^{20}$ and $R^{23}$ is a hydrogen atom or an alkyl group having 1 to 6 carbon atoms; and wherein $L^2$ is optionally a second linker, and wherein in (A2) s is a number from 0 to 2, t is a number from 1 to 6, and each B is a hydrogen atom, an alkyl group having 1 to 6 carbon atoms, or an aryl or substituted aryl group.

23. The active material of claim 22 wherein X is S, each of $R^1$ and $R^2$ is t-butyl, and $R^3$, $R^4$, $R^7$, $R^8$, $R^9$, and $R^{10}$ are each hydrogen.

24. The active material of claim 22 wherein X is $SO_2$, each of $R^1$ and $R^2$ is t-butyl, and $R^3$, $R^4$, $R^7$, $R^8$, $R^9$, and $R^{10}$ are each hydrogen.

25. The active material of claim 22 wherein X is a covalent bond, each of $R^1$ and $R^2$ is t-butyl, and $R^3$, $R^4$, $R^7$, $R^8$, $R^9$, and $R^{10}$ are each hydrogen.

26. The active material of claim 22 wherein (L) is —$CH_2$—$CH_2$—$CH_2$—.

27. The active material of claim 22 wherein (L) is phenyl.

28. The active material of claim 27 wherein structure (A2) is further defined as structure (A6):

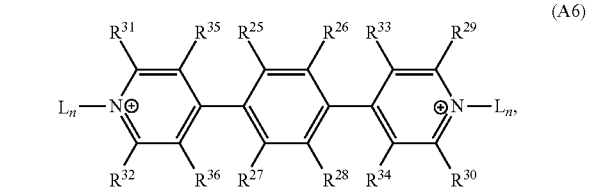

(A6)

wherein in (A6) $R^{25}$-$R^{36}$ is chosen from an alkyl group having from 1 to 4 carbon atoms, an alkyl ether group, an alkylammonium alkyl group, an oligoether group, a phenyl group, and hydrogen.

29. The redox flow battery of claim 28 wherein each of $R^{25}$-$R^{36}$ is hydrogen.

* * * * *